US012697441B2

(12) United States Patent
Cortinovis et al.

(10) Patent No.: US 12,697,441 B2
(45) Date of Patent: Aug. 4, 2026

(54) METHODS AND APPARATUS FOR ASPECTS OF A DOSE DETECTION SYSTEM

(71) Applicant: Eli Lilly and Company, Indianapolis, IN (US)

(72) Inventors: Marco Cortinovis, Seriate (IT); Bhakti Girish Khandagale, Indianapolis, IN (US); Rossano Claudio Massari, Lissone (IT)

(73) Assignee: Eli Lilly and Company, Indianapolis, IN (US)

( * ) Notice: Subject to any disclaimer, the term of this patent is extended or adjusted under 35 U.S.C. 154(b) by 1068 days.

(21) Appl. No.: 17/635,211

(22) PCT Filed: Aug. 19, 2020

(86) PCT No.: PCT/US2020/046937
§ 371 (c)(1),
(2) Date: Feb. 14, 2022

(87) PCT Pub. No.: WO2021/034902
PCT Pub. Date: Feb. 25, 2021

(65) Prior Publication Data
US 2022/0273886 A1      Sep. 1, 2022

Related U.S. Application Data

(60) Provisional application No. 62/889,813, filed on Aug. 21, 2019.

(51) Int. Cl.
*A61M 5/50*      (2006.01)
*A61M 5/315*      (2006.01)

(52) U.S. Cl.
CPC ...... *A61M 5/31568* (2013.01); *A61M 5/5086* (2013.01); *A61M 2205/14* (2013.01);
(Continued)

(58) Field of Classification Search
CPC .. A61M 2205/8206; A61M 2205/3306; A61M 5/5086; G01J 3/463; G01J 3/46
See application file for complete search history.

(56) References Cited

U.S. PATENT DOCUMENTS 5,748,104 A    5/1998  Argyroudis et al.
5,854,994 A    12/1998  Canada et al.
(Continued)

FOREIGN PATENT DOCUMENTS

| DE | 112008003576 | T5 | | 1/2011 | |
|---|---|---|---|---|---|
| EP | 3017734 | B1 | | 5/2016 | |
| KR | 101683266 | B1 | * | 12/2016 | ........... G01N 21/534 |
| WO | 2009098392 | A1 | | 8/2009 | |
| WO | 2010098928 | | | 9/2010 | |
| WO | 2012046199 | A1 | | 4/2012 | |
| WO | 2014161952 | A1 | | 10/2014 | |
| WO | 2014173770 | A1 | | 10/2014 | |

(Continued)

OTHER PUBLICATIONS

P. Deurenberg, "Achieving color point stability in RGB multi-chip LED modules using various color control loops", 2005 (Year: 2005).*

(Continued)

*Primary Examiner* — Maurice C Smith
(74) *Attorney, Agent, or Firm* — M. Daniel Spillman

(57) ABSTRACT

The techniques described herein relate to computerized methods and apparatus of at least one of for determining whether a dose sensing module is attached to a medication delivery device, such as, for example, with dose detection sensors, for detecting a color of a portion of a medication delivery device to determine a medication contained in the medication delivery device, such as, for example, with a set of LEDs and light sensor for different temperature conditions, and for monitoring a battery life of a battery in the dose sensing module, such as, for example, with current/ voltage detection for different temperature conditions. At least some of the information obtained from these techniques may be communicated to a paired remote electronic device, such as a user's smartphone.

14 Claims, 17 Drawing Sheets

(52) U.S. Cl.
CPC .............. *A61M 2205/3313* (2013.01); *A61M 2205/3317* (2013.01); *A61M 2205/3368* (2013.01); *A61M 2205/3553* (2013.01); *A61M 2205/6081* (2013.01); *A61M 2205/8206* (2013.01)

(56) References Cited

U.S. PATENT DOCUMENTS

| | | | |
|---|---|---|---|
| 6,216,096 B1 | 4/2001 | Obermeier | |
| 6,695,210 B2 | 2/2004 | Watanabe et al. | |
| 6,798,517 B2 | 9/2004 | Wagner et al. | |
| 6,999,890 B2 | 2/2006 | Kai | |
| 7,291,132 B2 | 11/2007 | DeRuntz et al. | |
| 7,322,955 B2 | 1/2008 | Azizi et al. | |
| 7,416,540 B2 | 8/2008 | Edwards et al. | |
| 7,461,584 B2 | 12/2008 | Blanc et al. | |
| 7,874,426 B2 | 1/2011 | Castellani | |
| 8,147,426 B2 | 4/2012 | Neel et al. | |
| 8,181,849 B2 | 5/2012 | Bazargan et al. | |
| 8,390,796 B2 | 3/2013 | Honda et al. | |
| 8,556,865 B2 | 10/2013 | Krulevitch et al. | |
| 8,560,271 B2 | 10/2013 | Koehler et al. | |
| 8,682,066 B2 | 3/2014 | Milgrom et al. | |
| 8,751,215 B2 | 6/2014 | Tardif | |
| 8,771,233 B2 | 7/2014 | Watanabe et al. | |
| 8,817,258 B2 | 8/2014 | Whalley et al. | |
| 8,894,611 B2 | 11/2014 | Larsen et al. | |
| 8,900,190 B2 | 12/2014 | Chong et al. | |
| 8,951,472 B2 | 2/2015 | Kellner et al. | |
| 9,015,072 B2 | 4/2015 | Wu et al. | |
| 9,101,723 B2 | 8/2015 | Larsen | |
| 9,125,991 B2 | 9/2015 | Schabbach et al. | |
| 9,152,829 B2 | 10/2015 | Day et al. | |
| 9,351,604 B2 | 5/2016 | Talon et al. | |
| 9,352,119 B2 | 5/2016 | Burkholz et al. | |
| 9,452,256 B2 | 9/2016 | Tieck et al. | |
| 9,550,021 B2 | 1/2017 | Beden et al. | |
| 9,568,432 B2 | 2/2017 | Baxi et al. | |
| 9,672,328 B2 | 6/2017 | Saint et al. | |
| 9,715,620 B2 | 7/2017 | Lysenkov et al. | |
| 9,782,543 B2 | 10/2017 | Groeschke et al. | |
| 9,782,544 B2* | 10/2017 | Heumann ............... | A61M 5/28 |
| 9,870,492 B2 | 1/2018 | Day et al. | |
| 10,016,567 B2 | 7/2018 | Denyer et al. | |
| 10,085,643 B2 | 10/2018 | Bandic et al. | |
| 10,117,999 B2 | 11/2018 | Andersen et al. | |
| 10,143,830 B2 | 12/2018 | Bochenko | |
| 10,155,090 B2 | 12/2018 | Larsen et al. | |
| 10,159,798 B2 | 12/2018 | Blei et al. | |
| 10,169,536 B2 | 1/2019 | Klemm et al. | |
| 10,173,020 B2 | 1/2019 | Sutherland et al. | |
| 10,183,128 B2 | 1/2019 | Wurmbauer et al. | |
| 10,258,745 B2 | 4/2019 | Despa et al. | |
| 10,306,193 B2 | 5/2019 | Weber et al. | |
| 10,331,996 B2 | 6/2019 | Schneider et al. | |
| 10,384,013 B2 | 8/2019 | Krusell et al. | |
| 10,398,852 B2 | 9/2019 | Taylor et al. | |
| 10,420,895 B2 | 9/2019 | Erbstein et al. | |
| 10,441,731 B2 | 10/2019 | Aoki et al. | |
| 10,446,269 B2 | 10/2019 | Groeschke et al. | |
| 10,460,836 B2 | 10/2019 | Andersen | |
| 10,471,213 B2 | 11/2019 | Schabbach et al. | |
| 10,471,216 B2 | 11/2019 | Kuhn et al. | |
| 10,518,039 B2 | 12/2019 | Mirov et al. | |
| 10,569,028 B2 | 2/2020 | Bitton et al. | |
| 10,625,022 B2 | 4/2020 | Rehbein et al. | |
| 10,632,256 B2 | 4/2020 | Sasaki | |
| 10,653,847 B2 | 5/2020 | Steel et al. | |
| 10,653,852 B2 | 5/2020 | Bauss et al. | |
| 10,657,403 B2 | 5/2020 | Klemm | |
| 10,661,013 B2 | 5/2020 | Bauss et al. | |
| 10,682,469 B2 | 6/2020 | Jakobsen et al. | |
| 10,695,504 B2 | 6/2020 | Nielsen et al. | |
| 10,722,658 B2 | 7/2020 | Byerly et al. | |
| 10,754,927 B2 | 8/2020 | Mensinger et al. | |
| 10,773,032 B2 | 9/2020 | Cirillo et al. | |
| 10,794,936 B2 | 10/2020 | Romero | |
| 10,799,649 B2 | 10/2020 | Marlin et al. | |
| 10,800,600 B2 | 10/2020 | Jarisch et al. | |
| 10,857,303 B2 | 12/2020 | Arenas Latorre et al. | |
| 10,874,802 B2 | 12/2020 | Toporek et al. | |
| 10,921,895 B2 | 2/2021 | Diaz et al. | |
| 10,956,538 B2 | 3/2021 | Mirov | |
| 10,980,943 B2 | 4/2021 | Gylleby et al. | |
| 10,987,472 B2 | 4/2021 | Byerly et al. | |
| 11,064,969 B2 | 7/2021 | Erkamp et al. | |
| 11,071,831 B2 | 7/2021 | Bauer et al. | |
| 11,141,541 B2 | 10/2021 | Richards et al. | |
| 11,197,963 B2 | 12/2021 | Helmer et al. | |
| 2005/0038407 A1 | 2/2005 | Sumka | |
| 2005/0085277 A1 | 4/2005 | Chen et al. | |
| 2006/0087497 A1 | 4/2006 | Borgaonkar et al. | |
| 2006/0097997 A1 | 5/2006 | Borgaonkar et al. | |
| 2006/0173417 A1 | 8/2006 | Rosen et al. | |
| 2008/0169307 A1 | 7/2008 | Hofstetter | |
| 2008/0245236 A1 | 10/2008 | Ternite et al. | |
| 2009/0174395 A1 | 7/2009 | Thomas et al. | |
| 2012/0078216 A1 | 3/2012 | Smith et al. | |
| 2012/0127290 A1 | 5/2012 | Tojo et al. | |
| 2012/0150114 A1 | 6/2012 | Krogh et al. | |
| 2014/0005950 A1 | 1/2014 | Groeschke et al. | |
| 2014/0194826 A1 | 7/2014 | Nielsen et al. | |
| 2014/0276583 A1 | 9/2014 | Chen et al. | |
| 2015/0356273 A1 | 12/2015 | Cave | |
| 2016/0001016 A1 | 1/2016 | Poulsen et al. | |
| 2016/0074593 A1 | 3/2016 | Heumann et al. | |
| 2016/0084986 A1 | 3/2016 | Zach et al. | |
| 2016/0231074 A1 | 8/2016 | McDaniel et al. | |
| 2016/0307336 A1 | 10/2016 | Allen | |
| 2016/0316113 A1 | 10/2016 | Zannier et al. | |
| 2017/0119962 A1 | 5/2017 | Fazi, Jr. | |
| 2017/0232204 A1 | 8/2017 | Knapp et al. | |
| 2018/0147362 A1 | 5/2018 | Arenas et al. | |
| 2018/0207366 A1 | 7/2018 | Marcoz et al. | |
| 2018/0280607 A1 | 10/2018 | Richards et al. | |
| 2019/0022328 A1 | 1/2019 | Schleicher et al. | |
| 2019/0192778 A1 | 6/2019 | Rehbein et al. | |
| 2019/0307965 A1 | 10/2019 | Wang et al. | |
| 2020/0147318 A1 | 5/2020 | Antonelli et al. | |
| 2020/0164160 A1 | 5/2020 | Helmer | |
| 2020/0171246 A1 | 6/2020 | Byerly et al. | |
| 2020/0206431 A1 | 7/2020 | Antonelli et al. | |
| 2020/0276390 A1 | 9/2020 | Song et al. | |
| 2021/0060260 A1 | 3/2021 | Ruiz-Valdepenas et al. | |
| 2021/0295517 A1* | 9/2021 | Parrish .................. | G01J 5/0846 |

FOREIGN PATENT DOCUMENTS

| | | | |
|---|---|---|---|
| WO | 2016135236 A1 | 9/2016 | |
| WO | 2016142727 A1 | 9/2016 | |
| WO | 2016193229 A1 | 12/2016 | |
| WO | 2018009509 | 1/2018 | |
| WO | 2018013419 A1 | 1/2018 | |
| WO | 2018036938 | 3/2018 | |
| WO | 2018036938 A1 | 3/2018 | |
| WO | 2018104292 A1 | 6/2018 | |
| WO | 2018138542 A1 | 8/2018 | |
| WO | 2018160425 A1 | 9/2018 | |
| WO | 2019001919 A1 | 1/2019 | |
| WO | 2019057911 A1 | 3/2019 | |
| WO | 2019057916 A1 | 3/2019 | |
| WO | 2019110494 A1 | 6/2019 | |
| WO | 2019121452 A1 | 6/2019 | |

OTHER PUBLICATIONS

Patent Cooperation Treaty International Search Report of the International Searching Authority pertaining to International Application No. PCT/US2020/46937; International Filing Date: Aug. 19, 2020; Date of Mailing: Apr. 14, 2021.
Patent Cooperation Treaty Written Opinion of the International Searching Authority pertaining to International Application No.

(56)          References Cited

OTHER PUBLICATIONS

PCT/US2020/46937; International Filing Date: Aug. 19, 2020; Date of Mailing: Apr. 14, 2021.
Lyons, "Quadrature Signals: Complex, But Not Complicated", 2008, Richard Lyons, 17 pages.
Lyons, "Quadratursignale: Komplex, aber nicht kompliziert", 2011, Horst Gruchow, DL6KBF, 17 pages.
"Skalierung des Ausgangssignals ", ME-Meßsysteme GmbH, May 23, 2015, Hennigsdorf, Germany, 10 pages, including English machine translation.

* cited by examiner

300

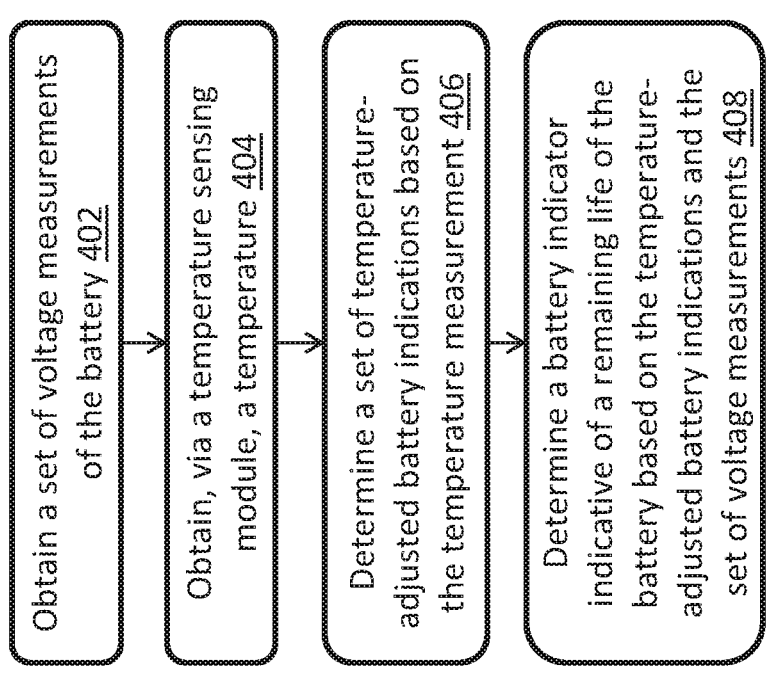

400

Obtain a set of voltage measurements of the battery 402

Obtain, via a temperature sensing module, a temperature 404

Determine a set of temperature-adjusted battery indications based on the temperature measurement 406

Determine a battery indicator indicative of a remaining life of the battery based on the temperature-adjusted battery indications and the set of voltage measurements 408

FIG. 4

Obtain a set of voltage measurements from each sensing element 1302

Determine two-dimensional data representative of magnetic field 1304

Determine one-dimensional data based on the two-dimensional data 1306

Determine, based on the one-dimensional data, whether the apparatus is coupled to the medication delivery device 1308

1300

METHODS AND APPARATUS FOR ASPECTS OF A DOSE DETECTION SYSTEM

TECHNICAL FIELD

The present disclosure relates to techniques for an electronic dose detection system for a medication delivery device, and in particular to techniques for detecting a connection to a medication delivery device, determining the type of medication delivery device, and monitoring battery life.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices. In other embodiments, there is a need for such a dose detection device to be integral with the delivery device.

It is also important to deliver the correct medication. A patient may need to select either a different medication, or a different form of a given medication, depending on the circumstances. If a mistake is made as to which medication is in the medication delivery device, then the patient will not be properly dosed, and records of dose administration will be inaccurate. The potential for this happening is substantially diminished if a dose detection device is used which automatically confirms the type of medication contained by the medication delivery device.

SUMMARY

The present disclosure relates to techniques for a dose sensing module that can be removably attached to a medication delivery device. The techniques can include determining whether the dose sensing module is attached to the medication delivery device. Such techniques can, for example, ensure that the dose sensing module only senses, processes, and/or reports events detected when attached to a medication delivery device (as opposed to accidental activation when the dose sensing module is not coupled to a medication delivery device), and can be used to determine when the dose sensing module is changed to a new medication delivery device. The techniques can also include detecting the color of a portion of a medication delivery device to determine the medication contained in the medication delivery device. Such techniques can, for example, ensure a patient is administering the correct medication to avoid mistakes as to which medication is in the medication delivery device. The techniques can further include monitoring the battery life of the battery in the dose sensing module. Such techniques can, for example, allow a user or patient to monitor the battery life in a manner that allows the patient to know well-ahead of time, in a reliable manner, when the battery will die so that the user or patient can properly plan ahead.

BRIEF DESCRIPTION OF THE DRAWINGS

Additional embodiments of the disclosure, as well as features and advantages thereof, will become more apparent by reference to the description herein taken in conjunction with the accompanying drawings. The components in the figures are not necessarily to scale. Moreover, in the figures, like-referenced numerals designate corresponding parts throughout the different views.

FIG. 4 is a flow chart of an exemplary computerized method for determining a battery indication, according to some embodiments.

DETAILED DESCRIPTION

Figure 1A:
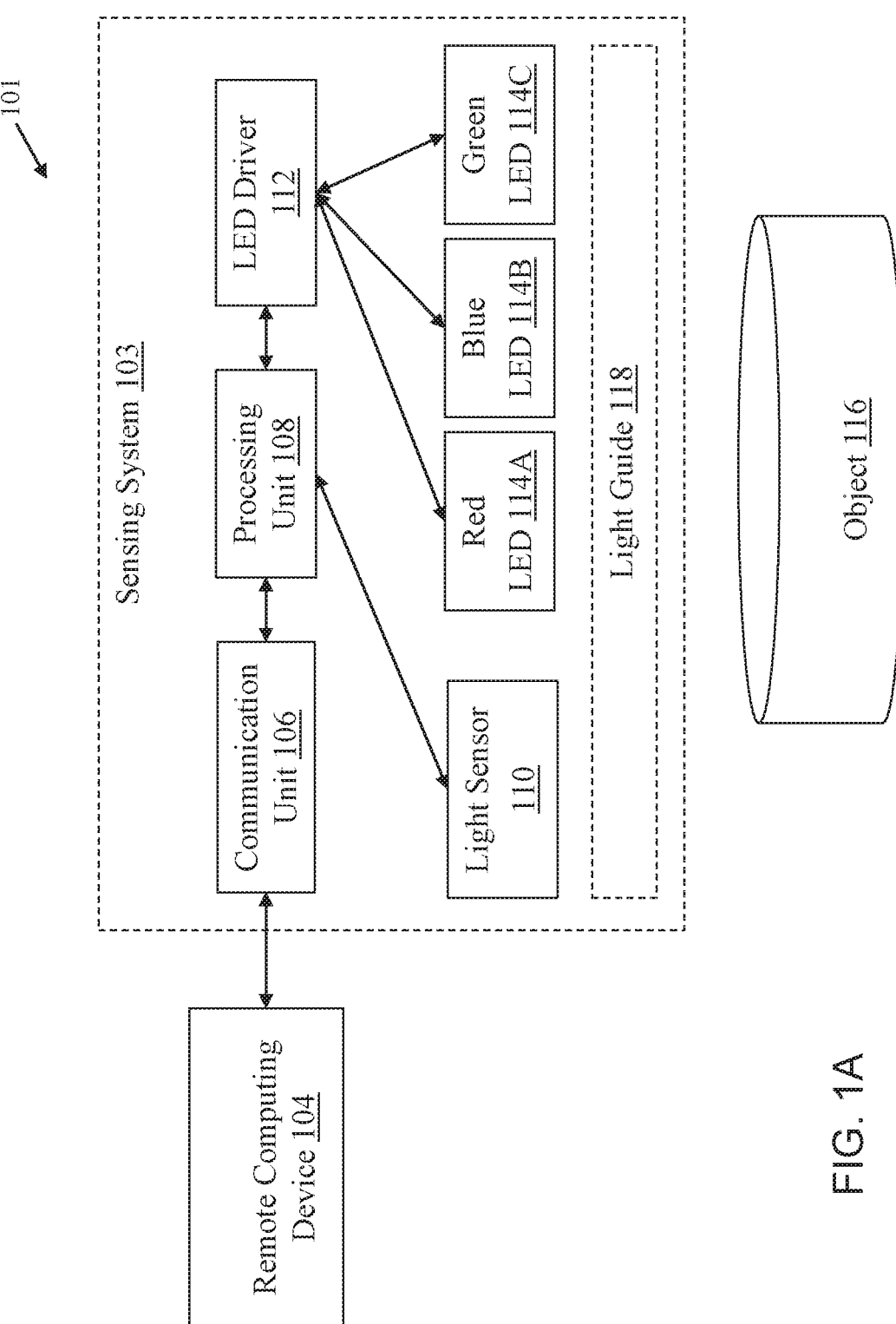
FIG. 1A is a diagram of an exemplary system, according to some embodiments.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining whether the sensing system is mounted to a medication delivery device. The inventors have discovered and appreciated that it can be desirable to have a dose sensing system be removably coupled to a medication delivery device. However, the inventors have discovered and appreciated that given the various hardware, firmware and/or software desired to be included in such dose sensing systems, and a desire to keep the dose sensing system small, user friendly, and limited to only include components with a low likelihood of failure due to repeated use, it can be challenging to also incorporating additional components (e.g., switches, latches, and/or the like) to detect when the dose sensing system is connected to a medication delivery device. The techniques described herein provide for leveraging existing components of the dose sensing device to determine whether the dose sensing device is coupled to a medication delivery device. For example, a dose sensing device can include sensors (such as Hall effect sensors) and related hardware and/or software to determine the size of a dose administered by the medication delivery device. The techniques can leverage such hardware and/or software used to perform dose detection to also determine whether (or not) the dose sensing system is coupled to a medication delivery device.

In a second aspect, the sensing system is for determining the type of medication contained within the medication delivery device. As described herein, the inventors discovered and appreciated that issues can occur without being able to determine the medication within the medication delivery device. For example, an incorrect medication can be administered to a patient, which can result in an improper patient dosing, cause incorrect dose administration records, and/or the like. The techniques described herein provide for sensing the color of a component of the medication being administered by the medication delivery device, where the color is indicative of the type of medication. In some embodiments, the techniques leverage one or more light emitting diodes and a light sensor to illuminate the applicable colored component and process the illumination data to match the color to a stored set of colors and associated medications.

In a third aspect, the sensing system is for monitoring the battery life of the sensing system. The inventors discovered and appreciated that determining the remaining battery life of a battery is complicated by various factors, such as temperature, relaxation time, duration of use, load variation, battery brand, battery variability, and other parameters. The inventors developed techniques to monitor the battery based on the dose sensing device architecture and in a manner that incorporates other relevant data, such as temperature. The techniques can provide for battery life estimations that adjust the measurement process in a manner that avoids errors that could otherwise be caused by existing battery measurement techniques.

By way of illustration, the medication delivery device is described in the form of a pen injector. However, the medication delivery device may be any device which is used to set and to deliver a dose of a medication, such as an infusion pump, bolus injector or an auto injector device. The medication may be any of a type that may be delivered by such a medication delivery device.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Devices described herein, such as a device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

FIG. 1A is a diagram of an exemplary system 120, according to some embodiments. The system 101 includes a sensing system 103 in communication with a remote computing device 104 through the communication unit 106 (e.g., via a wired and/or wireless connection). The communication unit 106 can be, for example, a WiFi transceiver, a Bluetooth transceiver, an RFID transceiver, a USB transceiver, a near-field communication (NFC) transceiver, a combination chip, and/or the like.

As described further herein, the sensing system 103 can be configured to determine illumination data indicative of a color of an object. The sensing system 103 includes a processing unit 108 (e.g., an MCU), in communication with a light sensor 110 and a control unit 112. The light sensor 110 is in optical communication with the object 116 (e.g., a portion of a medication delivery device). In some embodiments, the light sensor 110 is an Ambient Light Sensor (ALS), e.g., working in reflective mode. The LED driver 112 is in communication with a set of light emitting diodes (LEDs) 114A, 114B and 114C (collectively LEDs 114) in optical communication with the object 116. For example, the LEDs 114 can include a red LED, a blue LED, and/or a green LED. The light sensor 110, the LEDs 114, or both, are optionally in optical communication with the object 116 through an optional light guide 118. The light guide 118 can be a transparent light guide, such as a Makrolon 2458 LightGuide. In some embodiments, the color sensor is made of separate LEDs, a single package RGB LEDs, or a combination thereof.

Figure 1B:
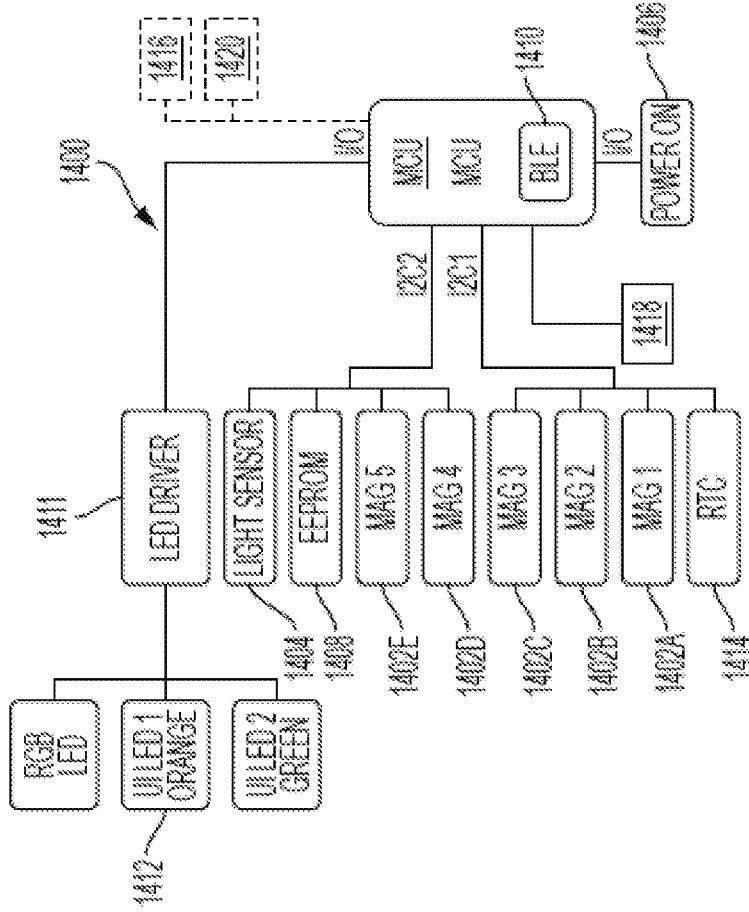
FIG. 1B depicts a block diagram of the controller and its components, according to some embodiments.

FIG. 1B illustrates a detailed example of the electronics assembly of the sensing module, referred to as 1400, which can be included in any of the modules described herein. MCU is programmed to achieve the electronic features of the module. MCU includes control logic operative to perform the operations described herein, including detecting a connection to a medication delivery device, determining the type of medication delivery device, obtaining data used for determining a dose delivered by a medication delivery device, and monitoring the battery life of the medication delivery device. The MCU may be operable to obtain data by detecting and/or determining the amount of rotation of the rotation sensor fixed to the flange, which is determined by detecting the magnetic field of the rotation sensor by the sensing elements of the measurement sensor, such as, for example, Hall Effect sensors, of the system.

Assembly 1400 includes MCU that can be operably coupled to one or more of dose sensors 1402A-E, memory 1408, identification sensor 1404, counter 1414, light driver 1411 and light indicators 1412, power-on module 1406, communication module 1410, display driver/display 1416, power source 1418, and presence module 1420. Assembly 1400 may include any number of dose sensors, such as, for example, five magnetic sensors 1402A-E (shown) or six sensors. The dose sensors can be used to determine the total units of rotation of components within the medication delivery device that can be used to determine an administered dose amount (e.g., as discussed further herein in conjunction with FIGS. 5-12), and can also be used to detect a connection to the medication delivery device. MCU may be configured via the presence module 1420, shown in this embodiment to be optional by dashed lines, to determine via the triggering of the presence switch system whether the module is coupled to the device's button. MCU is configured to determine the color of the dose button via the identification sensor 1404, and in some examples, associate the color data determined onboard, or off board with an external device (e.g., remote computing device 104), the color corresponding to a particular medication (e.g., using the LEDs 114, as discussed further herein). MCU is configured to determine triggering of the wake-up switch in order to power on the electronic assembly for use, shown as power-on module 1406. In one example, the total rotation may be communicated to an external device that includes a memory having a database, look up table, or other data stored in memory to correlate the total rotational units to an amount of medication delivered for a given medication identified. In another example, MCU's may be configured to determine the amount of medication delivered. MCU may be operative to store the detected dose in local memory 1408 (e.g., internal flash memory or on-board EEPROM). MCU is further operative to wirelessly transmit a signal representative of device data, such as, for example, (any one or any combination thereof) the rotational units, medication identification (such as color) data, timestamp, time since last dose, battery charge status, module identification number, time of module attachment or detachment, time of inactivity, and/or other errors (such as for example dose detection and/or transmission error, medication identification detection and/or transmission error), to a paired remote electronic device, such as a user's smartphone, over a Bluetooth low energy (BLE) or other suitable short or long-range wireless communication protocol module 1410, such as, for example, near-field communication (NFC), WiFi, or cellular network. Illustratively, the BLE control logic and MCU are integrated on a same circuit. In one example, any of the modules described herein may include the display module 1420, shown in this embodiment to be optional by dashed lines, for indication of information to a user. Such a display, which may be LEDs, LCD, or other digital or analog displays, may be integrated with proximal portion finger pad. MCU includes a display driver software module and control logic operative to receive and processed sensed data and to display information on said display, such as, for example, dose setting, dosed dispensed, status of injection, completion of injection, date and/or time, or time to next injection. In another example, MCU includes a LED driver 1411 coupled to one or more LEDS 1412, such as, for example, RGB LED, Orange LED and Green LED, used to communicate by sequences of on-off and different colors to the patient of whether data was successfully transmitted, whether the battery charge is high or low, or other clinical communications. Counter 1414 is shown as a real time clock (RTC) that is electronically coupled to the MCU to track time, such as, for example, dose time. Counter 1414 may also be a time counter that tracks seconds from zero based on energization. The time or count value may be communicated to the external device.

In some embodiments, as discussed further in conjunction with FIGS. 8-12, the sensing system 103 is configured to be connected to a medication delivery device. In some embodiments, the object 116 is a portion of a medication delivery device (e.g., a button, a label, a color of an external compartment, etc.) that can be used to identify an aspect of the medication delivery device based on the color of the object 116. For example, the color of the object 116 can be indicative of a type of medication of the medication delivery device.

Figure 1C:
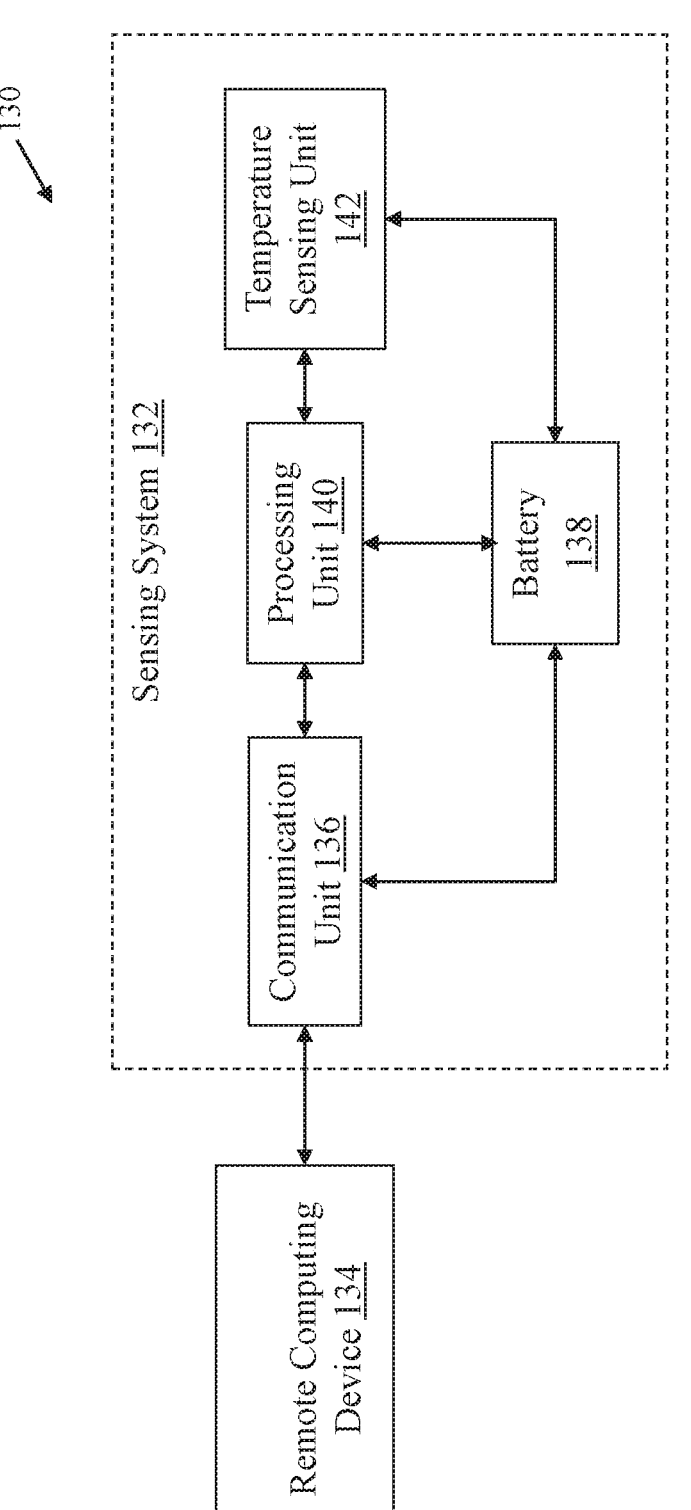
FIG. 1C is a diagram of an exemplary system, according to some embodiments.

FIG. 1C is a diagram of an exemplary system 130, according to some embodiments. The system 130 includes aspects of a dose detection system, including sensing system 132 in communication with a remote computing device 134 through the communication unit 136 (e.g., via a wired and/or wireless connection). As described further herein, the sensing system 132 can be configured to determine a battery indicator indicative of a remaining life of the battery 138. The apparatus 132 includes a processing unit 140 in communication with the communication unit 136, the battery 138 and the temperature sensing unit 142.

The exemplary aspects of a dose detection system described in conjunction with FIGS. 1A-1C are shown for exemplary purposes to highlight various aspects of dose detection systems. Aspects shown in FIGS. 1A-1C can be combined into a single apparatus, such as the dose delivery detection system 80 described in conjunction with FIGS. 8-12, and can be implemented using, for example, the various exemplary configurations discussed in conjunction with those figures.

Referring to FIG. 1A, in some embodiments, the sensing system 103 is configured to determine the color of the object (e.g., the button of a pen medication delivery device). In some embodiments, the sensing system determines the object color by switching on in sequence the LEDs 114, and reading back the reflected beams through a wide spectra ambient light sensor 110. The sensing system 103 can generate various values, such as three values for each of three LEDs 114. The sensing system 103 can process the generated values to generate a final color value for matching. The sensing system 103 can check the final color value against a predefined set of colors to determine whether there is a match.

Figure 2:
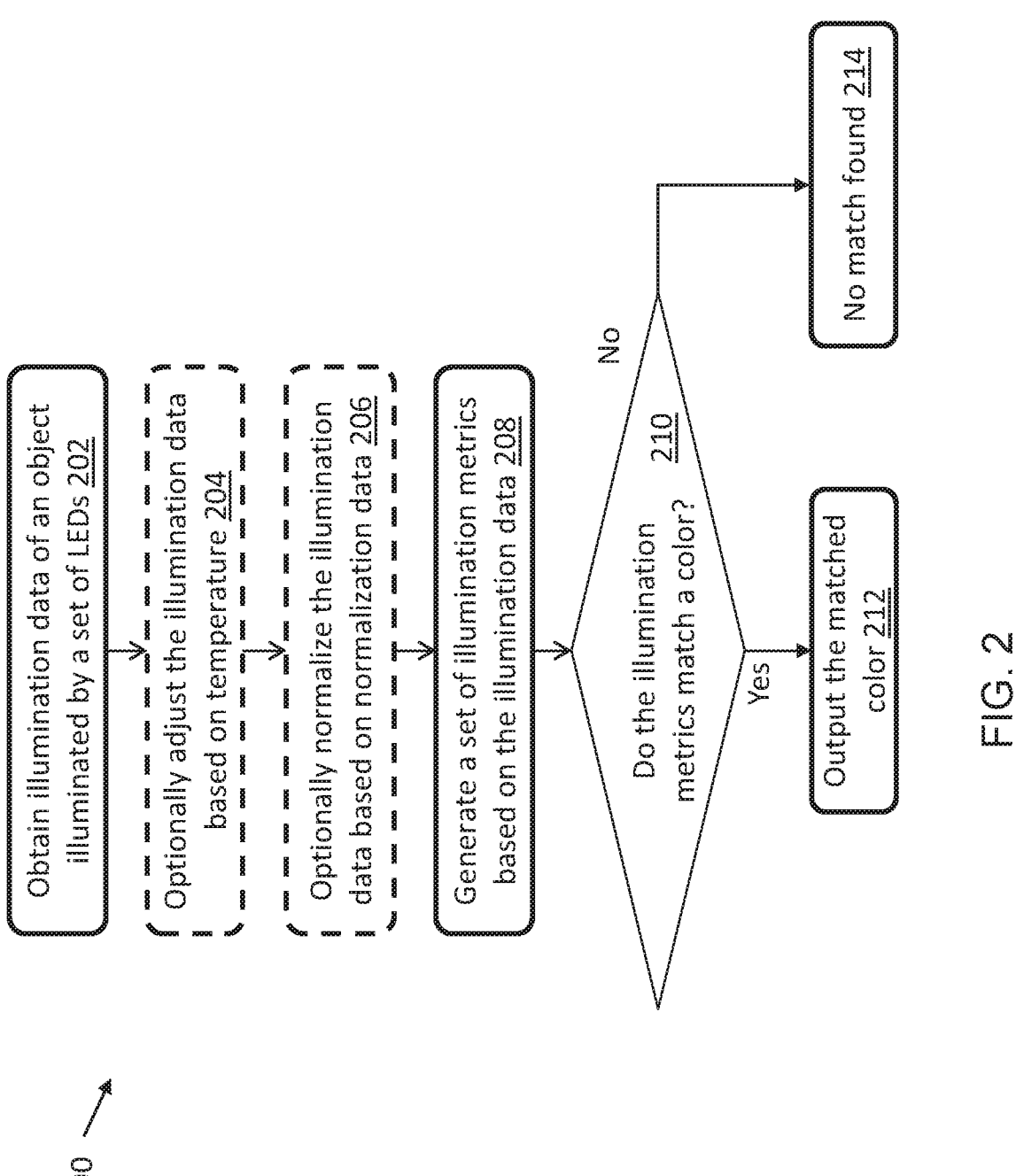
FIG. 2 is a flow chart of an exemplary computerized method for determining a color associated with an object, according to some embodiments.

FIG. 2 is a flow chart of an exemplary computerized method 200 for determining a color associated with an object, according to some embodiments. A processor, such as the processing unit 108 of the sensing system 103, can execute computer readable instructions that cause the processor to perform the method 200. At step 202, the sensing system obtains illumination data of an object illuminated by a set of LEDs. The sensing system can optionally process the illumination data at steps 204 and/or 206 to generate processed illumination data. At step 204, the sensing system optionally adjusts the illumination data based on the temperature. At step 206, the sensing system optionally normalizes the illumination data. At step 208, the sensing system causes the light sensor to capture illumination data of the object while the object is illuminated by the set of LEDs. At step 208, the sensing system transmits the processed illumination data to a remote device (e.g., via a communication module in communication with the processor of the apparatus). At step 210, the remote device determines whether the illumination metrics match a stored set of colors. If the remote device determines a match, at step 212 the remote device outputs the matched color (e.g., to a program, to a display, etc.). If the remote device does not determine a match, at step 214 the remote device outputs that a color match was not found (e.g., by returning an error code, a no match code, and/or the like).

Referring to step 202, the sensing system can be configured to capture first illumination data when the object is not illuminated by the set of LEDs, second illumination data when the object is illuminated by each LED of the set of LEDs, or both. For example, the apparatus can be configured to capture illumination data for the object when the object is illuminated just by ambient light when the LEDs are not turned on. In some embodiments, the sensing system can include an exposure time during which to capture the dark illumination data.

As another example, if the set of LEDs comprises different color LEDs, the apparatus can be configured to capture illumination data of the object when the object is illuminated by each LED. For example, as shown in FIG. 1A, in some embodiments the apparatus includes a red LED 114A, a blue LED 114B, and a green LED 114C. The apparatus can be configured to coordinate the light sensor 110 and the LED driver 112 to coordinate lighting the LEDs 114 and capturing illumination data such that the light sensor 110 captures illumination data when the object is illuminated by the red LED 114A (and not the other LEDs), illumination data when the object is illuminated by the blue LED 114B, and illumination data when the object is illuminated by the green LED 114C. In some embodiments, the sensing system can be configured to use an exposure time during which to capture the illumination data, which can be the same for each LED and/or different for one or more LEDs.

Referring to step 204, the illumination data can be adjusted based on temperature. In some embodiments, the temperature is taken of the ambient air, the sensing system, and/or of the medication delivery device. In some embodiments, the sensing system can capture a plurality of temperature measurements and average the values to determine and averaged temperature to use for adjusting the illumination data. In some embodiments, the sensing system can adjust each illumination data value (X) using Equation 1:

$$\text{rgbTempX}=\text{rgb}X*(1-\text{TempCoefficient}X*(\text{Temp}-\text{CalTemp})) \quad \text{(Equation 1)}$$

Where:
- rgbTempX is the adjusted illumination data value determined for each color, such as a red value, a green value, and a blue value, depending on which color Equation 1 is being computed for;
- rgbX is each original illumination data value, such as a red value, a green value, and a blue value;
- TempCoefficientX is a temperature coefficient for each value, which can allow the various temperature measurements to be tracked using one coefficient (e.g., since there may be performance drift in different temperature measurements);
- CalTemp is a temperature measured during calibration of the sensing system, which can be used to account for temperature variation (e.g., for non-calibration measurements); and
- Temp is the measured (e.g., averaged) temperature.

Referring to step 206, the sensing system can normalize the (temperature adjusted) illumination data based on the dark illumination data captured without illumination of the LEDs. In some embodiments, the sensing system can normalize the illumination data based on one or more illumination measurements determined during calibration. For example, Equation 2 can be used to normalize each illumination data value (X):

$$bNormX = \frac{rgbTempX - blackX + \frac{(calDark - darkValue)*expTimeX}{darkExpTime}}{whiteX - blackX} * 10000 \quad \text{(Equation 2)}$$

Where:
- bNormX is the normalized illumination value, such as the red, green or blue normalizated value, depending on which color Equation 2 is being computed for (in percent, multiplied by 100);
- whiteX represents illumination values, such as the red, green and blue values, obtained during the calibration phase when using a white target object (described further in conjunction with FIG. 3);
- blackX represents illumination values, such as the red, green and blue values, obtained during the calibration phase when using a black target object (described further in conjunction with FIG. 3);
- calDark is a dark illumination value (with the LEDs off) determined during the calibration phase (described further in conjunction with FIG. 3); and
- darkValue is the dark illumination value determined during step 202.

Referring to step 210, the remote device can be configured to determine lightness A B (LABc) values. The system can determine the LABc values based on any of the illumination values, whether it be the raw illumination data or illumination data that is temperature adjusted and/or normalized illumination data. For illustrative purposes, the following examples refer to normalized illumination data for simplicity. The A value can be calculated depending on the normalized illumination values. For example, depending on whether rgbNormRed determined using Equation 2 is greater than rgbNormGreen, then one of either Equations 3 or 4 is used to determine the A value:

$$A = Kn * \left( \frac{rgdNormRed}{rgbNormGreen} - 1 \right) \quad \text{if } rgbNormRed > rgbNormGreen \qquad \text{(Equation 3)}$$

$$A = -Kn * \left( \frac{rgbNormGreen}{rgbNormRed} - 1 \right) \quad \text{if } rgbNormRed \le rgbNormGreen \qquad \text{(Equation 4)}$$

The B value can also be calculated depending on the normalized illumination values. For example, depending on whether rgbNormBlue determined using Equation 2 is greater than rgbNormGreen, then one of either Equations 5 or 6 is used to determine the B value. For equations 3-6, Kn is a coefficient used for the RGB to LABc transformation so that the A and B values will be in the range of −100 to 100, and that L is in the range 0 to 100 (e.g., 20, 21.5, 23, etc.).

$$B = -Kn * \left( \frac{rgdNormBlue}{rgbNormGreen} - 1 \right) \quad \text{if } rgbNormBlue > rgbNrmGreen \qquad \text{(Equation 5)}$$

$$B = Kn * \left( \frac{rgdNormGreen}{rgbNormBlue} - 1 \right) \quad \text{if } rgbNormBlue \le rgbNrmGreen \qquad \text{(Equation 6)}$$

The L value can be calculated using Equation 7:

$$L = \sqrt{\frac{rgbNormRed + rgbNormGreen + rgbNormBlue}{3}} \qquad \text{(Equation 7)}$$

In some embodiments, the remote device can include a table of metrics used for determining whether the illumination data meets a color. The remote device can include a set of colors (e.g., grey, blue, dark blue, red, and/or other colors), where each color has an associated set of data. The data associated with each color can include average data and/or sigma variation data determined during calibration and/or design of the system. In some embodiments, each color can include an average for each of the A, B and L values and a sigma variation value for each of the A, B and L values. The remote device can determine the sigma distance for the illumination data and each color in the stored set of colors. For example, Equation 8 can be used to determine the sigma distance for each color in the set of colors:

$$SigmaDistanceX =$$
$$= \sqrt{\left( \frac{L - \mu LX}{\sigma LX} \right)^2 + \left( \frac{A - \mu AX}{\sigma AX} \right)^2 + \left( \frac{B - \mu BX}{\sigma BX} \right)^2} \qquad \text{(Equation 8)}$$

Where:
SigmaDistanceX is the sigma distance for the color (X) under consideration from the set of colors;
For the real-time measurement:
L is calculated using Equation 7;
A is calculated using either Equation 3 or 4;
B is calculated using either Equation 5 or 6;
For the color (X) under consideration:
$\mu LX$ is the average of the L value for color (X);
$\sigma LX$ is the sigma variation of the L value for color (X);
$\mu AX$ is the average of the A value for color (X);
$\sigma AX$ is the sigma variation of the A value for color (X);
$\mu BX$ is the average of the B value for color (X); and $\sigma BX$ is the sigma variation of the B value for color (X).

The remote device can determine whether the illumination data matches a color in the set of colors using the sigma distances. For example, the remote device can select the minimum among the sigma distance values (Min1) as the most likelihood matched color. The second smallest value (Min2) can be used for a match color check, as discussed further herein.

The sensing system and/or remote device can be configured to perform one or more checks for the illumination data. For example, the dark illumination data can be checked to determine whether the subsequent measurements under LED illumination are interfered with by ambient light. As another example, the acquired illumination data for the LEDs can be checked to ensure the illumination data is within an expected threshold between a lowest black value and a highest white value. As a further example, the LABc values can be checked to determine whether they are within acceptable ranges (e.g., −100 to 100 for A or B, 0 to 100 for L). As another example, a match color check can be performed to ensure that Min1 and/or Min2 are within acceptable values. For example, Min1 can be checked to ensure Min1 is below a maximum sigma distance for an expected color match, and/or the ratio of Min2/Min1 can be compared to a minimum ratio between the two minimum values for an acceptable match.

Figure 3:
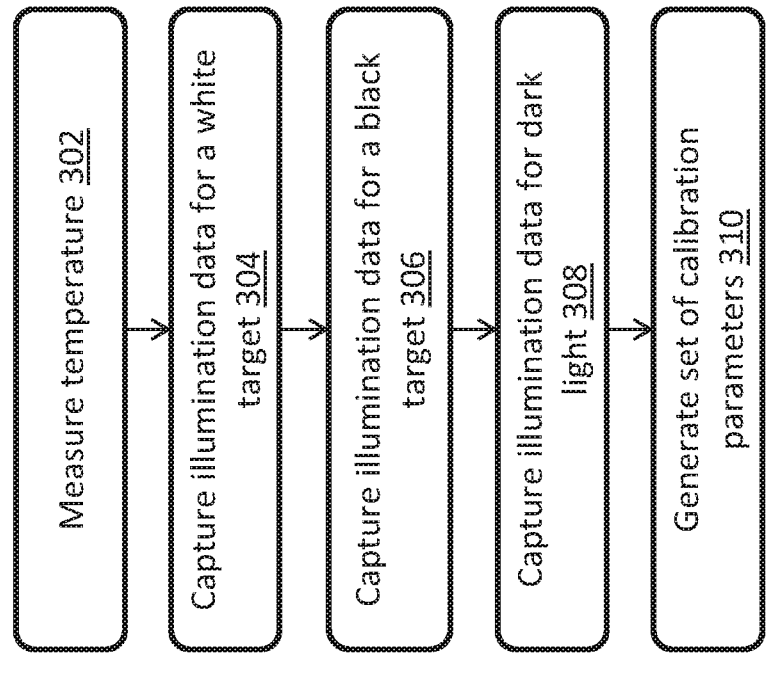
FIG. 3 is a flow chart of an exemplary computerized method for generating calibration parameters, according to some embodiments.

During calibration, the sensing device can take various measurements that can be used to calibrate the real-time measurements of an object. The calibration measurements can include the temperature and various light measurements, such as measurements using a white target, a black target, and dark illumination without any LEDs on. FIG. 3 is a flow chart of an exemplary computerized method 300 for generating calibration parameters, according to some embodiments. At step 302, the apparatus measures the temperature. At step 304, the apparatus captures illumination data for a white target object (e.g., a white object). At step 306, the apparatus captures illumination data for a black target (e.g., a black object). At step 308, the apparatus captures illumination data for dark light without the LEDs on. At step 310, the apparatus generates a set of calibration parameters. The calibration parameters can include an exposure time (or maximum/minimum exposure times) to use for dark measurement and/or for each LED (e.g., for red, green and blue LEDs), counts read during calibration for each LED for each of the white and/or black object, temperature, a temperature margin, and/or other calibration parameters.

As described herein, the dose sensing system includes a sensing module with various components, including a processor/MCU, sensors, LEDs, among other components. In some embodiments, the sensing module can be powered by a battery. Referring to FIG. 1C, for example, the sensing system 132 includes a battery 138 that powers the dose sensing system, including the exemplary components shown in FIG. 1C. The techniques described herein can be used to monitor the battery life of a dose sensing system. The battery life can be monitored to provide information to a user, such as a battery status indicator that tracks the life of the battery, alerts related to the battery (e.g., to alert the user to a low battery life, when to change the battery, etc.), and/or the like. For example, the dose sensing system can alert the user, whether it be through the sensing module or a remote computing device, when the battery will run out in a manner that provides the user with sufficient time to replace the battery (e.g., one or two weeks prior to the end of life of the battery).

The inventors have discovered and appreciated that estimating battery life, such as by using battery voltage measurements, can be complicated due to the fact that the battery behavior can depend on a number of variables, such as temperature, relaxation time from measure to measure, duration of an injection of an attached medication delivery device, load variation, battery brand, battery variability, and other parameters. To address such issues, which are often not controllable by the device provider, the inventors have developed techniques to monitor the battery based on the device architecture in a manner that provides sufficient margin on the battery life to compensate for the potential error(s) and variabilities that the inventors have appreciated can otherwise occur during battery measurement.

FIG. 4 is a flow chart of an exemplary computerized method 400 for determining a battery indication, according to some embodiments. A processor, such as the processing unit 140 of the apparatus 132 in FIG. 1B, can be configured to execute computer readable instructions that cause the processor to perform the method 400. At step 402, the apparatus obtains a set of voltage measurements of the battery. At step 404, the apparatus obtains a temperature measurement (e.g., via the temperature sensing module). At step 406, the apparatus determines a set of temperature-adjusted battery indications based on the temperature measurement. At step 408, the apparatus determines a battery indicator indicative of a remaining life of the battery based on the temperature-adjusted battery indications and the set of voltage measurements.

Referring to step 402, the apparatus (e.g., the MCU) can obtain various voltage measurements when the battery is under different loads and/or at different operating states of the apparatus. In some embodiments, the apparatus obtains (a) a startup battery voltage when the apparatus is powered on, (b) a high current battery voltage when the processor is running at a maximum speed, (c) a low current battery voltage when the processor is running in a low-power mode, or some combination thereof. The startup battery voltage can be determined, for example, by obtaining a high current battery voltage within a certain amount of time from the sensing module being powered on. For example, when the apparatus is woken up (e.g., following a button press) the apparatus may increase the draw from the battery. In some embodiments, when woken up the apparatus may initiate a boot process. The boot-up process may increase the draw from the battery due to, for example, various self-tests, the booting operation, and/or the like. In some embodiments, when woken up the apparatus may take magnetic measurements (e.g., to determine a starting position of one or more components). Such a boot-up process and/or magnetic sensing may therefore provide a high current battery voltage for measurement as the startup battery voltage.

The high current battery voltage can capture a high (e.g., maximum) current peak, e.g., which can be used to measure the voltage drop at that point. The high current battery voltage can be determined, for example, by running the microcontroller at maximum speed and all the other loads in low power mode for a predetermined time (e.g., in ms), and measuring the high current battery voltage. In some embodiments, the high current battery voltage is an average voltage computed based on a set of measurements. In some embodiments, the high current battery voltage can be calculated at the beginning of and/or at the end of the magnetic sensor activity. For example, a maximum voltage drop of the system may be obtained when the magnetic sensor(s) have completed a measurement.

The low current battery voltage can be used to measure the voltage drop with a lowest current load, e.g., to simulate an open circuit voltage check for the battery. The low current battery voltage can be determined, for example, by having the firmware running on the MCU put all the loads (e.g., including the MCU) in low power mode for a predetermined time (e.g., a rest period specified in ms), and measuring the low current battery voltage. In some embodiments, the low current battery voltage is an average voltage computed by averaging a set of measurements. In some embodiments, the low current battery voltage is determined after determining the high current battery voltage measurement.

As described herein, one or more voltage measurements can be used for step 402. For example, in some embodiments the voltages can be taken in a manner designed to obtain a voltage reading at a high and/or maximum current consumption (e.g., the point with a maximum voltage drop) and a representative open circuit voltage measurement for a low/lowest current consumption. The voltages can be used, as described herein, to estimate the remaining battery energy. In some embodiments, the techniques may use, for example, a single voltage drop, such as the maximum voltage drop, to estimate the remaining battery energy (e.g., since the maximum voltage drop may be more dependent on battery status compared to other voltage drops, which may be more capacitive driven). For example, the power-on/start-up voltage drop can simply be used for comparison with the maximum voltage drop. For example, if the voltage drop during power on is bigger than a measured maximum drop of the system, the comparison can indicate there is a risk that the component may reset.

Referring to step 406, the apparatus can store battery indication tables at various temperatures. For example, the apparatus can store a set of low temperature battery indications that includes a set of battery indications that each have an associated voltage for a low temperature. Table 1 is an example of a set of low temperature battery indications (e.g., at 0° C.):

TABLE 1

| Battery Indicator | Voltage (mV) |
| --- | --- |
| 100 | 2460 |
| 90 | 2334 |
| 80 | 2317 |
| 70 | 2310 |
| 60 | 2282 |
| 50 | 2242 |
| 40 | 2214 |
| 30 | 2176 |
| 20 | 2113 |
| 10 | 1998 |
| 4 | 1950 |

As another example, the apparatus can store a set of high temperature battery indications that includes a set of high temperature battery indications that each have an associated voltage for a high temperature. Table 2 is an example of a set of high temperature battery indications (e.g., at 22-24° C.):

TABLE 2

| Battery Indicator | Voltage (mV) |
| --- | --- |
| 100 | 2764 |
| 90 | 2710 |
| 80 | 2690 |
| 70 | 2663 |
| 60 | 2626 |

TABLE 2-continued

| Battery Indicator | Voltage (mV) |
|---|---|
| 50 | 2573 |
| 40 | 2514 |
| 30 | 2454 |
| 20 | 2388 |
| 10 | 2242 |
| 4 | 2050 |

The sensing system can determine, based on the set of low temperature battery indications, the set of high temperature battery indications, and the temperature measurement(s) obtained at step 402, a set of temperature-adjusted battery indications. In some embodiments, the sensing system (e.g., via firmware executing on the MCU) can determine a correction factor based on the temperature measured at step 404. For example, the sensing system can determine a correction factor based on the measured temperature and one or more correction factors. A logarithmic (shown below) and/or linear relationship may be developed to characterize the correction factor. For example, the sensing system can use Equation 9 to determine the correction factor:

$$corrFactor=A*\log_2(Temp+LogOffset)+Temp*B+C \quad \text{(Equation 9)}$$

Where:
corrFactor is the correction factor;
A, B and C are coefficients (e.g., determined based on collected data to provide a desired degrees of freedom for determining the correction factor); and
LogOffset is a coefficient (e.g., determined based on collected data to provide a desired degrees of freedom for determining the correction factor).

The sensing system can determine a corrected set of battery indications (e.g., a corrected battery table) based on the temperature correction factor. In some embodiments, the sensing system can determine the corrected battery indications based on both the low and high temperature battery table. For example, the sensing system can use Equation 10 to determine each corrected battery voltage associated with each indicator:

$$corrBatCurve_x=\{(Voltage_{TEMPHIx}-Voltage_{TEMPLOx})/ \\ (TEMPHI-TEMPLO)\}*(corrFactor-TEMPHI)+ \\ Voltage_{TEMPHIx} \quad \text{(Equation 10)}$$

Where:
corrBatCurve$_x$ is the corrected battery curve voltage for row X;
Voltage$_{TEMPHIx}$ is the voltage for row X in the high temperature battery table;
Voltage$_{TEMPLOx}$ is the voltage for row X in the low temperature battery table;
TEMPHI is the temperature used when determining the high temperature battery table;
TEMPLO is the temperature used when determining the low temperature battery table; and
corrFactor is the correction factor determined using Equation 9.

Referring to step 408, the apparatus can determine the battery indicator based on a previous battery indicator. For example, the apparatus can obtain the previous battery indicator for the battery, determine a current battery indicator for the battery based on the temperature-adjusted battery indications in the corrected battery table and the set of voltage measurements, and determine the battery indicator based on the previous battery indicator and the current battery indicator.

In some embodiments, the sensing system can determine the current battery indicator based on the stored battery tables and/or corrected battery table. For example, the sensing system can interpolate the points in the corrected battery table with the high current battery voltage (e.g., measured at step 402 in FIG. 4). For example, if the high current battery voltage is equal to a voltage value in the table, the sensing system can determine that the battery indicator is the associated indicator for that row. As another example, if the high current battery voltage is between two voltage values in the table, the sensing system can interpolate the two associated battery indicators to determine an associated battery indication.

In some embodiments, the sensing system can determine a new battery indicator based on the previous battery indicator (e.g., which can be stored in storage on the sensing system, such as in EEPROM). For example, the sensing system can use Equation 11 to determine the new battery indicator:

$$newBatInd=(FILTER*batInd+curBatInd)/(FILTER+1) \quad \text{(Equation 11)}$$

Where:
newBatInd is the new battery indicator;
batInd is the previous battery indicator (e.g., obtained from EEPROM);
curBatInd is the current determined battery indicator; and
FILTER is a filter value. FILTER can be determined based on the amount of time lapsed since the last operation associated with the sensing system (e.g., a communication sync with a remote computing device, such as remote computing device 104), a bonding event with a remote computing device, and/or detection of a dose administered by an associated medication delivery device).

The sensing system can store the determined new battery indicator (e.g., into EEPROM). In some embodiments, additional data can be stored with the new battery indicator, such as a timestamp, a number of remaining injections, and/or the like. For example, an initial injection number can be configured by the system that is associated with a new sensing system and/or new battery, and the sensing system can be configured to decrease the injection number for each sensed injection through the medication delivery device.

The apparatus of can transmit the battery indicator to a remote device (e.g., remote computing device 104). The remote device can process the new battery indicator. For example, the remote device can be configured to determine a battery status based on the battery indicator. As an example, the following Table 3 illustrates exemplary battery statuses and associated battery indicators:

TABLE 3

| Battery Indicator | Battery Status |
|---|---|
| 100 | Full |
| 90 | Full |
| 80 | Full |
| 70 | Full |
| 60 | Med |
| 50 | Med |
| 40 | Med |
| 30 | Med |
| 20 | Low |
| 10 | Low |
| 4 | Change Battery- Less than 120 injection remaining |
| 3 | Change Battery- Less than 90 injection remaining |

TABLE 3-continued

| Battery Indicator | Battery Status |
|---|---|
| 2 | Change Battery- Less than 60 injection remaining |
| 1 | Change Battery- Less than 30 injection remaining |
| 0 | EOL |

In some embodiments, the sensing device can enter a low battery state once the sensing device raises a low battery flag for the first time (e.g., when the device is unlikely to be able to provide more than a certain number of injections, such as 120 injections). The sensing device, once entering a low battery state, can avoid changing out of the low battery state for that battery (e.g., to avoid moving back-and-forth from a low battery state and a non-low battery state). In some embodiments, the sensing device can be configured to decrease the battery indicator by one for each new operation (e.g., a sync, bonding, or dose event) of the sensing device once it is in a low power state. In some embodiments, the sensing device can be configured to decrease the number of remaining injections by one for each new operation of the sensing device once it is in a low power state. Once the battery indicator equals zero, the sensing system can enter an end of life state. In some embodiments, the battery can be changed and the sensing system can reset upon detecting a new battery. In some embodiments, the sensing system is disposable and can be disposed upon reaching and end of life state.

In some embodiments, the sensing system can perform one or more checks on data obtained and/or measurements made during the battery monitoring processes. For example, the MCU can raise a low battery warning once the new battery indicator falls below a predetermined threshold. As another example, the sensing system can check whether sensed voltages are within predetermined acceptable ranges, whether temperature measurements are within predetermined acceptable ranges, and/or the like.

As described herein, the techniques can be used with various types of medication delivery devices, including medication delivery devices that incorporate the aspects described herein, as well as add-on components that can be attached to a medication delivery device. For illustrative purposes, FIGS. 5-12 describe exemplary medication delivery devices and dose sensing systems into which the techniques can be incorporated. Such techniques are discussed further in PCT Application No. PCT/US19/18780 filed on Feb. 20, 2019, which is hereby incorporated by reference herein.

Figure 5:
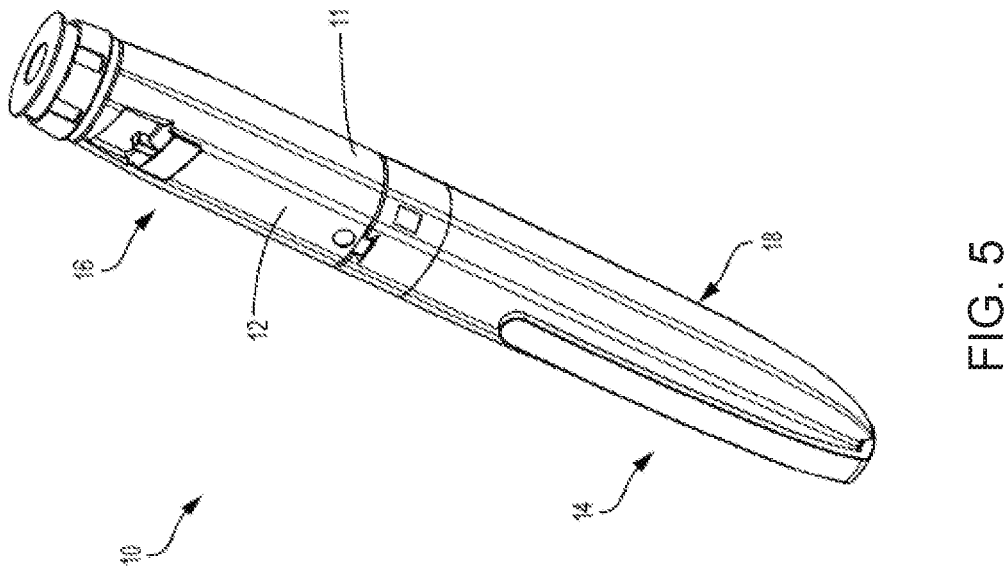
FIG. 5 is a perspective view of an exemplary medication delivery device with which the dose detection system of the present disclosure is operable.
Figure 6:
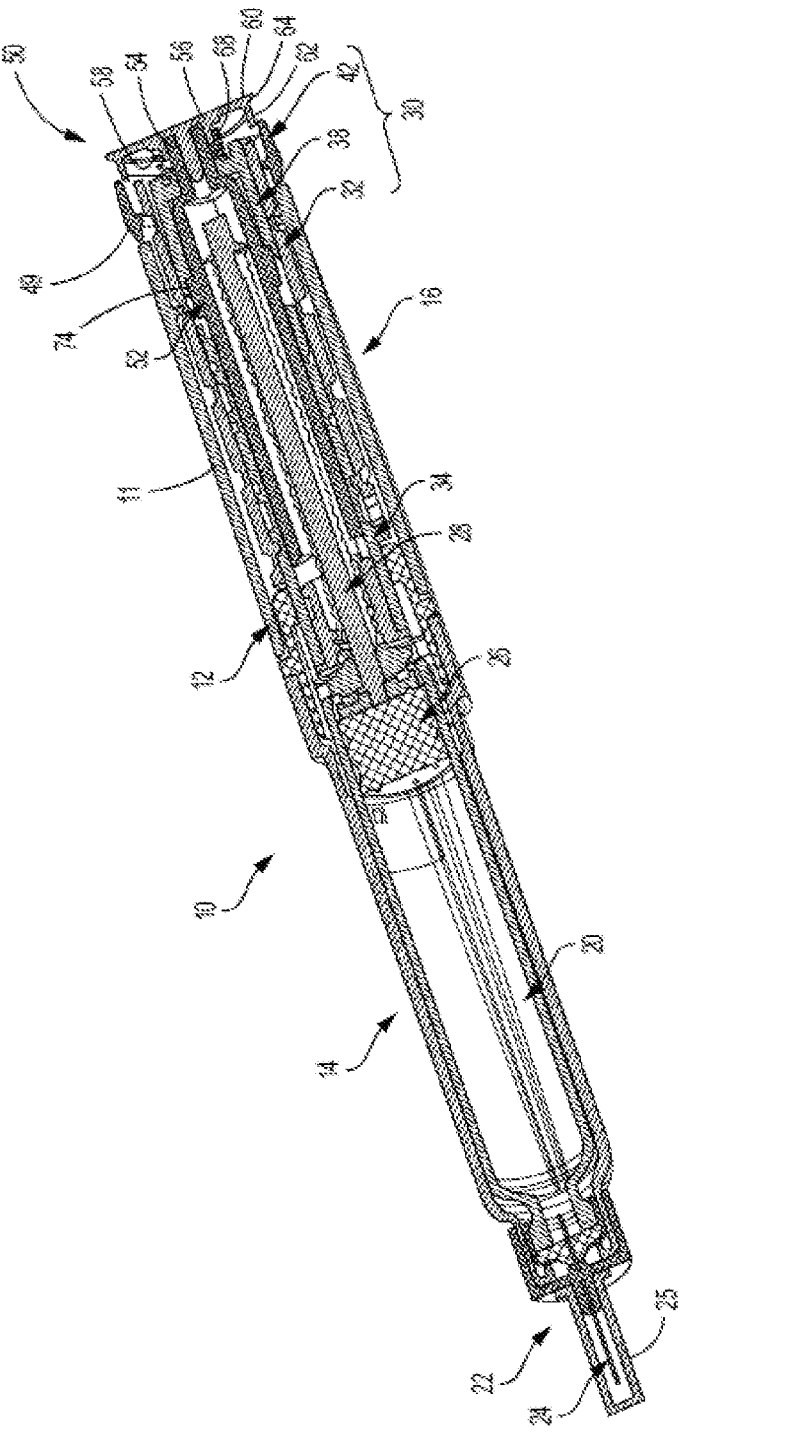
FIG. 6 is a cross-sectional perspective view of the exemplary medication delivery device of FIG. 5.

FIGS. 5-6 illustrate an exemplary medication delivery device 10, according to some examples. The medication delivery device 10 is a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 6, distal portion 14 contains the reservoir or cartridge 20 configured to hold the medicinal fluid of medication to be dispensed through its distal outlet end during a dispensing operation. The outlet end of distal portion 14 is equipped with a removable needle assembly 22 including an injection needle 24 enclosed by a removable cover 25. A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (e.g., simultaneously move axially and rotationally) relative to housing 12 during dose setting and dose dispensing. FIGS. 5 and 6 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Figure 7:
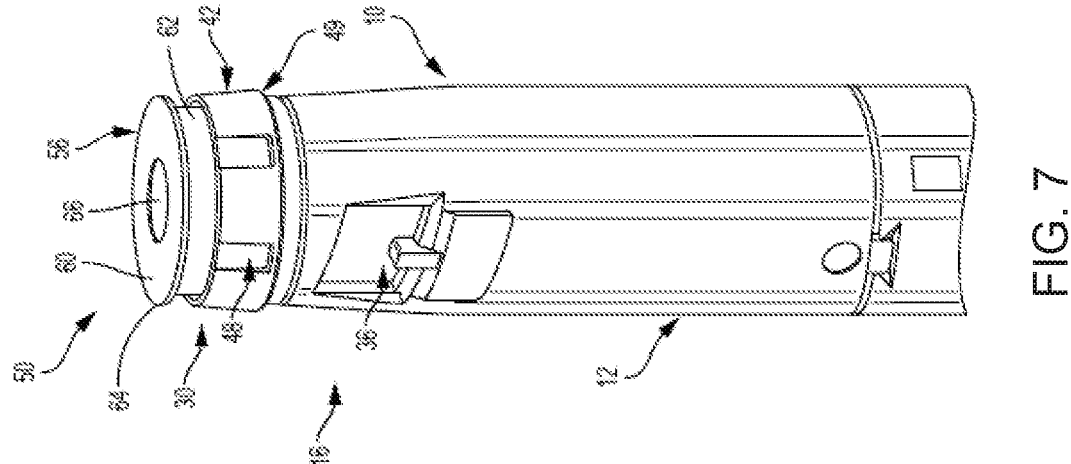
FIG. 7 is a perspective view of the proximal portion of the exemplary medication delivery device of FIG. 5.
Figure 8:
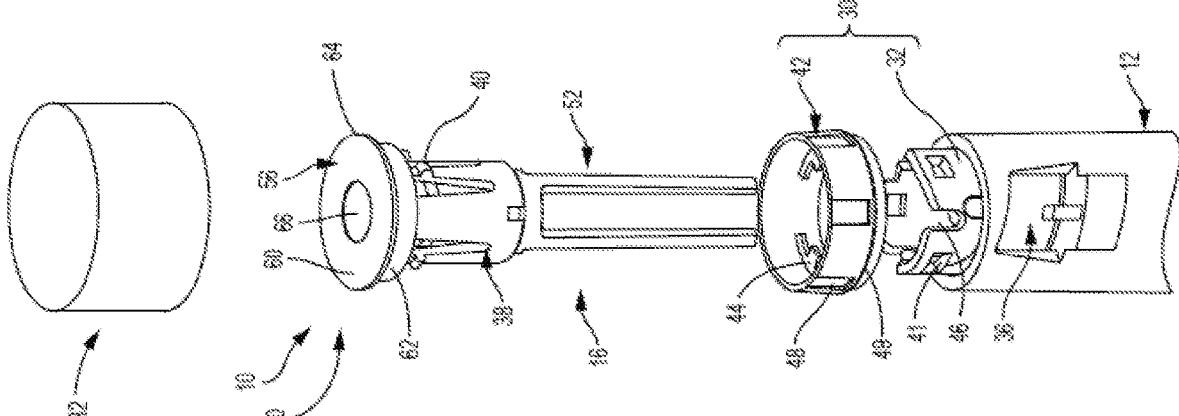
FIG. 8 is a partially-exploded, perspective view of the proximal portion of the exemplary medication delivery device of FIG. 5, together with a dose detection system of the present disclosure.

Referring to FIGS. 6-8, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 6) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dial member 32 by detents 40 received within openings 41 in dial member 32. Dose setting member 30 may further include a collar or skirt 42 positioned around the outer periphery of dial member 32 at its proximal end. Skirt 42 is axially and rotationally locked to dial member 32 by tabs 44 received in slots 46. Further embodiments described later shown examples of the device without a skirt.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dose dial member 32 and, as described later, cooperates with a clutch to selectively couple dial member 32 with a dose button 56. Skirt 42 provides a surface external of body 11 to enable a user to rotate the dial member 32 for setting a dose. For embodiments without the skirt, the dosage button 56 includes an outer wall that extends distally to form a surface to for the user to rotate.

Skirt 42 illustratively includes a plurality of surface features 48 and an annular ridge 49 formed on the outer surface of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose button 56 and/or dose dial member 32 for dose setting. In the embodiment of FIG. 8, a user may grasp and rotate the radial exterior surface of one-piece dose button 56, which also includes a plurality of surface features, for dose setting.

Delivery device 10 includes an actuator 50 having a clutch 52 which is received within dial member 32. Clutch 52 includes an axially extending stem 54 at its proximal end. Actuator 50 further includes dose button 56 positioned proximally of skirt 42 of dose setting member 30. Dose button 56 includes a mounting collar 58 (FIG. 6) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between. Proximal face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 6), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow back-driving rotation of dose setting member 30 relative to actuator 50 and housing 12. The dose dispensing mode of operation may also be initiated by activating a separate switch or trigger mechanism.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 6).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 6). Device 10 is then once again arranged in a ready state or zero dose position as shown in FIGS. 6 and 7.

The start and end angular positions of dose dial member 32, and therefore of the rotationally fixed flange 38 and skirt 42, relative to dose button 56 provide an "absolute" change in angular positions during dose delivery. Determining whether the relative rotation was in excess of 360° is determined in a number of ways. By way of example, total rotation may be determined by also taking into account the incremental movements of the dose setting member 30 which may be measured in any number of ways by a sensing system.

Various sensor systems are contemplated herein. In general, the sensor systems comprise a sensing component and a sensed component. The term "sensing component" refers to any component which is able to detect the relative position of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose delivery detection system, the sensed component rotates relative to the sensing component, which is able to detect the angular position and/or the rotational movement of the sensed component. For the dose type detection system, the sensing component detects the relative angular position of the sensed component. The sensing component may comprise one or more sensing elements, and the sensed component may comprise one or more sensed elements. The sensor system is able to detect the position or movement of the sensed component(s) and to provide outputs representative of the position(s) or movement(s) of the sensed component(s).

A sensor system typically detects a characteristic of a sensed parameter which varies in relationship to the position of the one or more sensed elements within a sensed area. The sensed elements extend into or otherwise influence the sensed area in a manner that directly or indirectly affects the characteristic of the sensed parameter. The relative positions of the sensor and the sensed element affect the characteristics of the sensed parameter, allowing a microcontroller unit (MCU) of the sensor system to determine different rotational positions of the sensed element.

Suitable sensor systems may include the combination of an active component and a passive component. With the sensing component operating as the active component, it is not necessary to have both components connected with other system elements such as a power supply or MCU.

Any of a variety of sensing technologies may be incorporated by which the relative positions of two members can be detected. Such technologies may include, for example, technologies based on tactile, optical, inductive or electrical measurements. Such technologies may include the measurement of a sensed parameter associated with a field, such as a magnetic field. In one form, a magnetic sensor senses the change in a sensed magnetic field as a magnetic component is moved relative to the sensor. In another embodiment, a sensor system may sense characteristics of and/or changes to a magnetic field as an object is positioned within and/or moved through the magnetic field. The alterations of the field change the characteristic of the sensed parameter in relation to the position of the sensed element in the sensed area. In such embodiments the sensed parameter may be a capacitance, conductance, resistance, impedance, voltage, inductance, etc. For example, a magneto-resistive type sensor detects the distortion of an applied magnetic field which results in a characteristic change in the resistance of an element of the sensor. As another example, Hall effect sensors detect changes in voltage resulting from distortions of an applied magnetic field.

In one aspect, the sensor system detects relative positions or movements of the sensed elements, and therefore of the associated members of the medication delivery device. The sensor system produces outputs representative of the position(s) or the amount of movement of the sensed component. For example, the sensor system may be operable to generate outputs by which the rotation of the dose setting member during dose delivery can be determined. MCU is operably connected to each sensor to receive the outputs. In one aspect, MCU is configured to determine from the outputs the amount of dose delivered by operation of the medication delivery device.

The dose delivery detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member during dose delivery. Thus, if the angular displacement is 90°, then 5 units of dose have been delivered.

One approach for detecting the angular displacement is to count increments of dose amounts as the injection proceeds. For example, a sensor system may use a repeating pattern of sensed elements, such that each repetition is an indication of a predetermined degree of angular rotation. Conveniently, the pattern may be established such that each repetition corresponds to the minimum increment of dose that can be set with the medication delivery device.

An alternative approach is to detect the start and stop positions of the relatively moving member, and to determine the amount of delivered dose as the difference between those positions. In this approach, it may be a part of the determination that the sensor system detects the number of full rotations of the dose setting member. Various methods for this are well within the ordinary skill in the art, and may include "counting" the number of increments to assess the number of full rotations.

The sensor system components may be permanently or removably attached to the medication delivery device. In an illustrative embodiment, as least some of the dose detection system components are provided in the form of a module that is removably attached to the medication delivery device.

This has the advantage of making these sensor components available for use on more than one pen injector.

In some embodiments, a sensing component is mounted to the actuator and a sensed component is attached to the dose setting member. The sensed component may also comprise the dose setting member or any portion thereof. The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery. The sensed component may also comprise the dose setting member or any portion thereof. In an illustrative embodiment, the rotation sensor is not attached directly to the relatively rotating dose setting member during dose delivery.

Figure 9:
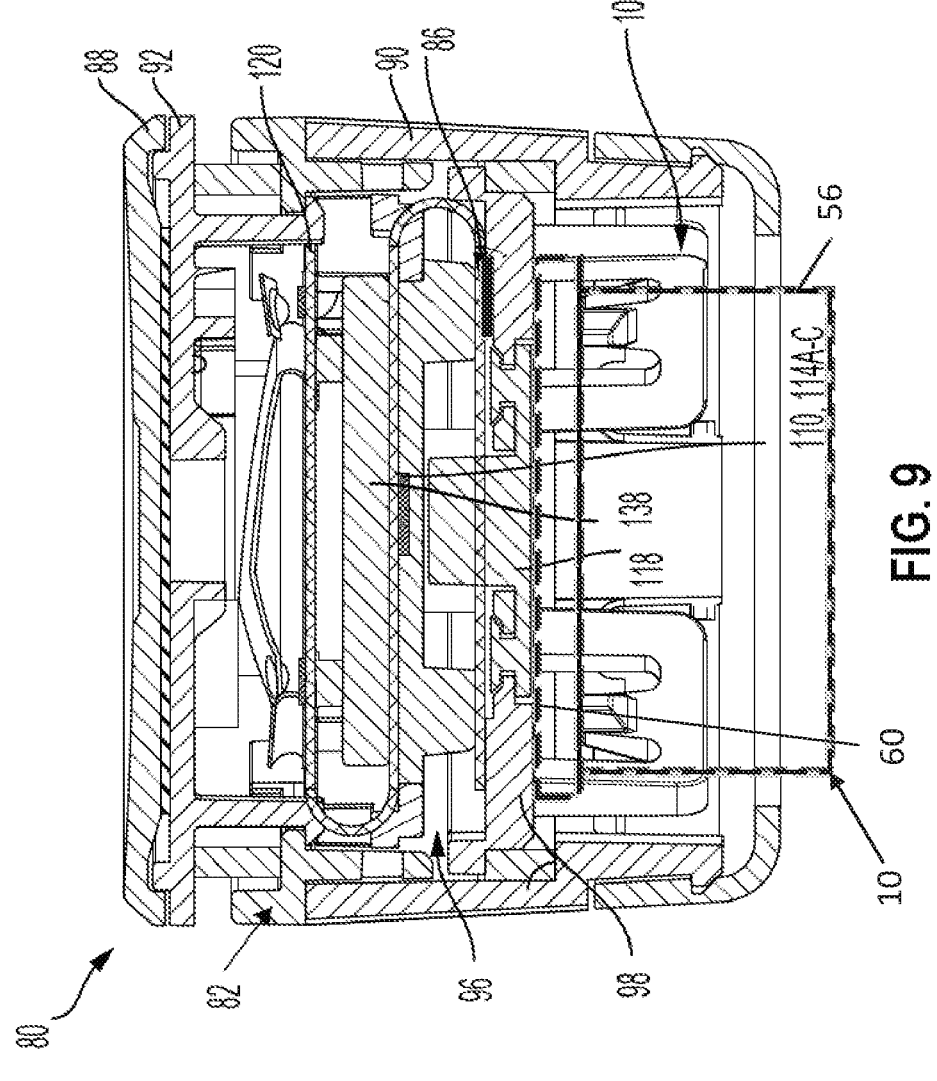
FIG. 9 is a side, diagrammatic view, partially in cross section, of a dose detection system module according to another exemplary embodiment attached to the proximal portion of a medication delivery device.
Figure 10A:
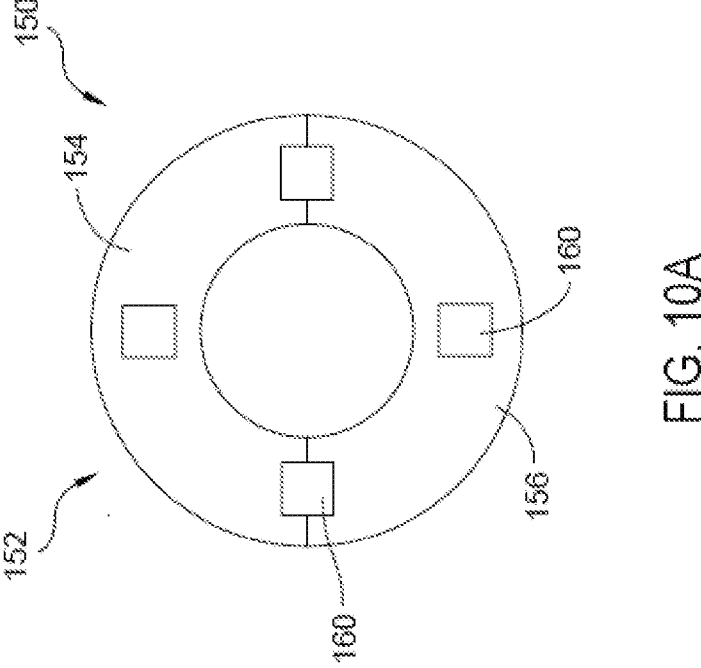
FIGS. 10A-B and 11A-B show yet other exemplary embodiments of dose detection systems utilizing magnetic sensing.
Figure 10B:
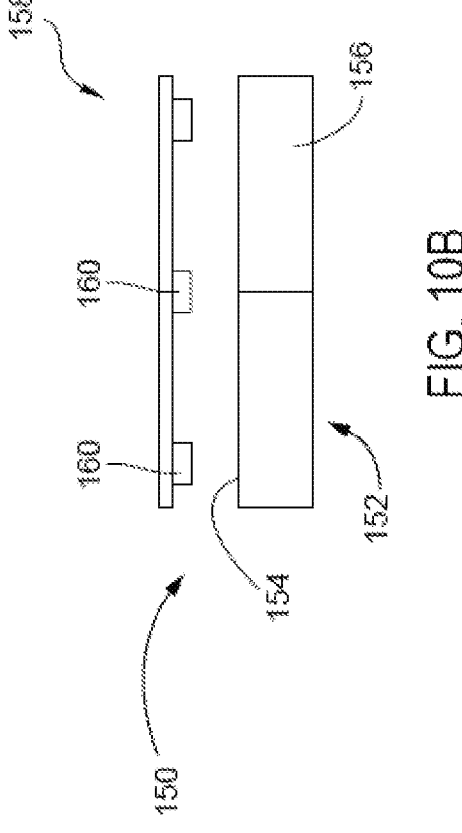

Referring to FIG. 9, there is shown in diagrammatic form a dose delivery detection system 80 including one example of a module 82 useful in combination with a medication delivery device, such as device 10. Module 82 carries a sensor system, shown generally at as a rotation sensor 86 (or more than one rotation sensor) and other associated components such as a processor, memory, battery, etc. Module 82 is provided as a separate component which may be removably attached to the actuator.

Dose detection module 82 includes a body 88 attached to dose button 56 (shown in dashed lines). Body 88 illustratively includes a cylindrical side wall 90 and a top wall 92, spanning over and sealing side wall 90. Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In the illustrative embodiment, module 82 is rotationally fixed with dose button 56 and does not rotate during dose delivery. This may be provided structurally, such as with tabs, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides a cavity 96 in which some or all of the rotation sensor and other components may be contained. Cavity 96 may be open at the bottom, or may be enclosed, such as by a bottom wall 98. Bottom wall 98 may be positioned in order to bear directly against face of dose button 56. Alternatively, bottom wall 98 if present may be spaced apart from dose button 56 and other contacts between module 82 and dose button 56 may be used such that an axial force applied to module 82 is transferred to dose button 56.

In another embodiment, module 82 may be rotationally fixed to the one-piece dose button configuration.

In an alternate embodiment, module 82 during dose setting is instead attached to dose setting member 30. For example, side wall 90 may include a lower wall portion 100 having inward projections in the form of coupling arms 102 that engage with button sidewall. In this approach, module 82 may effectively engage the proximal face 60 of dose button 56 and the distal side of annular ridge 49. In this configuration, lower wall portion 100 may be provided with surface features which engage with the surface features of dose button to rotationally fix module 82 with dose button. Rotational forces applied to housing 82 during dose setting are thereby transferred to dose button by virtue of the coupling of lower wall portion 100 with sidewall of the dose button. Light guide 118 is shown disposed between the LEDs 114A-C and light sensor 110, shown collectively at a single location of the electronics assembly, and the face of the dosage button 56 when present. Battery 138 is shown disposed above the light system 89 and part of the electronics assembly.

An exemplary electronics assembly 120 comprises a flexible printed circuit board (FPCB) having a plurality of electronic components. The electronics assembly comprises a sensor system including one or more rotation sensors 86 operatively communicating with a processor for receiving signals from the sensor representative of the sensed relative rotation. The electronics assembly further includes the MCU comprising at least one processing core and internal memory. One example of an electronics assembly schematic is shown in FIG. 1B.

Referring to FIGS. 10A, 10B, 11A, and 11B, there is shown an exemplary magnetic sensor system 150 including as the sensed element an annular, ring-shaped, bipolar magnet 152 having a north pole 154 and a south pole 156. Magnets described herein may also be referred to as diametrically magnetized ring. Magnet 152 is attached to flange 38 and therefore rotates with the flange during dose delivery. Magnet 152 may alternately be attached to dose dial 32 or other members rotationally fixed with the dose setting member. Magnet 152 may configured from a variety materials, such as, rare-earth magnets, for example, neodymium, and others.

Figure 11A:
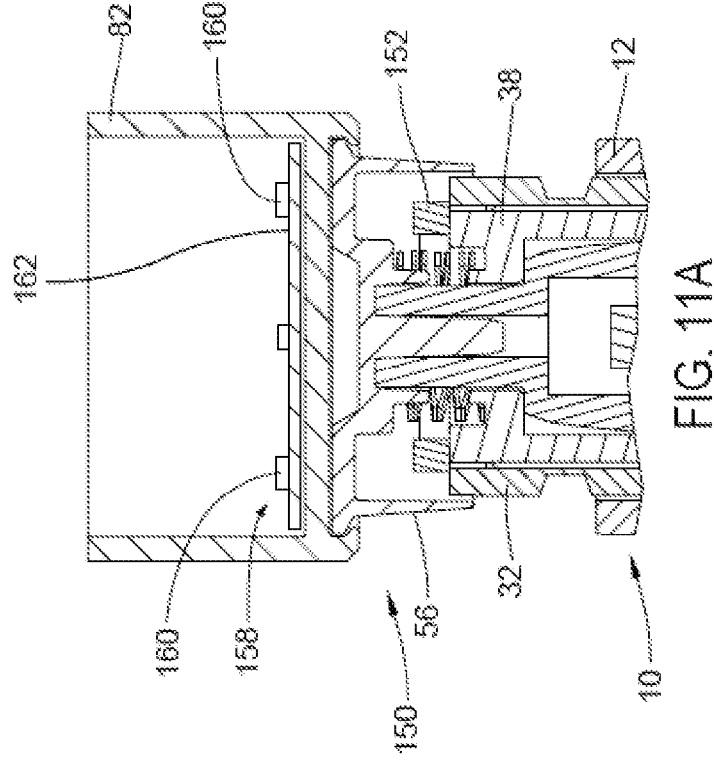

Sensor system 150 further includes a measurement sensor 158 including one or more sensing elements 160 operatively connected with sensor electronics (not shown) contained within module 82. The sensing elements 160 of sensor 158 are shown in FIG. 11A attached to printed circuit board 162 which is turn attached module 82, which is rotationally fixed to dose button 56. Consequently, magnet 152 rotates relative to sensing elements 160 during dose delivery. Sensing elements 160 are operable to detect the relative angular position of magnet 152. Sensing elements 160 may include inductive sensors, capacitive sensors, or other contactless sensors when the ring 152 is a metallic ring. Magnetic sensor system 150 thereby operates to detect the total rotation of flange 38 relative to dose button 56, and therefore the rotation relative to housing 12 during dose delivery. In one example, magnetic sensor system 150 including magnet 152 and sensor 158 with sensing elements 160 may be arranged in the modules.

Figure 11B:
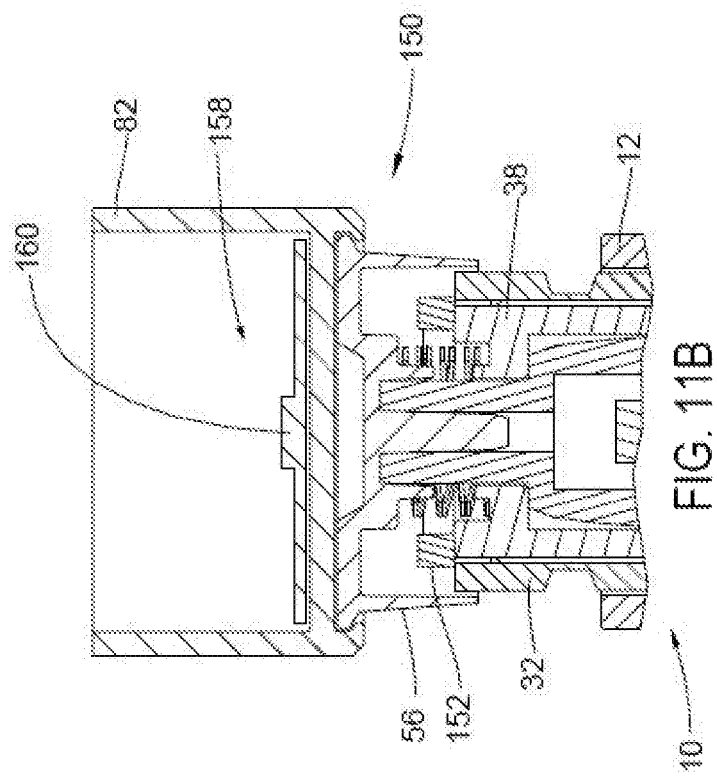

In one embodiment, magnetic sensor system 150 includes four sensing elements 160 equi-radially spaced within module 82 to define a ring pattern as shown. Alternative numbers and positions of the sensing elements may be used. For example, in another embodiment, shown in FIG. 11B, a single sensing element 160 is used. Further, sensing element 160 in FIG. 11B is shown centered within module 82, although other locations may also be used. In another embodiment, shown in FIG. 12, for example, five sensing elements 906 equi-circumferentially and equi-radially spaced within the module. In the foregoing embodiments, sensing elements 160 are shown attached within module 82. Alternatively, sensing elements 160 may be attached to any portion of a component rotationally fixed to dose button 56 such that the component does not rotate relative to housing 12 during dose delivery.

For purposes of illustration, magnet 152 is shown as a single, annular, bi-polar magnet attached to flange 38. However, alternative configurations and locations of magnet 152 are contemplated. For example, the magnet may comprise multiple poles, such as alternating north and south poles. In one embodiment the magnet comprises a number of pole pairs equaling the number of discrete rotational, dose-setting positions of flange 38. Magnet 152 may also comprise a number of separate magnet members. In addition, the magnet component may be attached to any portion of a member rotationally fixed to flange 38 during dose delivery, such as skirt 42 or dose dial member 32.

Alternatively, the sensor system may be an inductive or capacitive sensor system. This kind of sensor system utilizes a sensed element comprising a metal band attached to the flange similar to the attachment of the magnetic ring described herein. Sensor system further includes one or more sensing elements, such as the four, five, six or more independent antennas or armatures equi-angularly spaced along the distal wall of the module housing or pen housing. These antennas form antenna pairs located 180 degrees or other degrees apart and provide a ratio-metric measurement of the angular position of metal ring proportional to the dose delivered.

The metal band ring is shaped such that one or more distinct rotational positions of metal ring relative to the module may be detected. Metal band has a shape which generates a varying signal upon rotation of metal ring relative to antennas. Antennas are operably connected with electronics assembly such that the antennas function to detect positions of metal ring relative to sensors, and therefore relative to housing 12 of pen 10, during dose delivery. Metal band may be a single, cylindrical band attached to the exterior of the flange. However, alternate configurations and locations of the metal band are contemplated. For example, the metal band may comprise multiple discrete metal elements. In one embodiment the metal band comprises a number of elements equal to the number of discrete rotational, dose-setting positions of flange. The metal band in the alternative may be attached to any portion of a component rotationally fixed to flange 38 during dose delivery, such as dial member 32. The metal band may comprise a metal element attached to the rotating member on the inside or the outside of the member, or it may be incorporated into such member, as by metallic particles incorporated in the component, or by over-molding the component with the metal band. MCU is operable to determine the position of the metal ring with the sensors.

MCU is operable to determine the start position of magnet 152 by averaging the number of sensing elements 160 (for example, four) at a maximum sampling rate according to standard quadrature differential signals calculation. During dose delivery mode, sampling at a targeted frequency is performed by MCU to detect the number of revolutions of magnet 152. At end of dose delivery, MCU is operable to determine the final position of magnet 152 by averaging the number of sensing elements 160 (for example, four) at a maximum sampling rate according to standard quadrature differential signals calculation. MCU is operable to determine from calculation of the total rotational angle of travel from the determined start position, number of revolutions, and the final position. MCU is operable to determine the number of dose steps or units by dividing the total rotational angle of travel by a predetermined number (such as 10, 15, 18, 20, 24) that is correlated with the design of device and medication.

Figure 12:
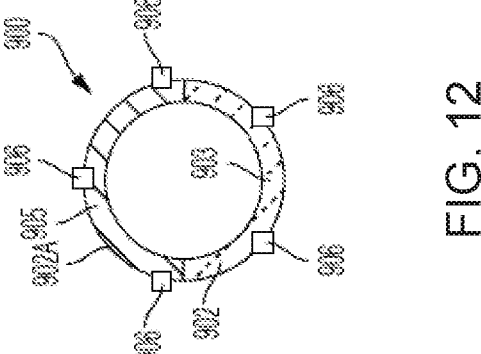
FIG. 12 is an axial view of yet other exemplary embodiment of the dose delivery detection system utilizing magnetic sensing.

Referring further to FIG. 12, FIG. 12 illustrates another example of a magnetic sensor system 900, including as the sensed element the diametrically magnetized ring 902 having the north pole 903 and the south pole 905. Magnetized ring 902 is attached to the dose setting member, such as, for example the flange, as previously described. The radial placement of the magnetic sensors 906, such as, for example, hall-effect sensors, relative to the magnetized ring 902, can be in an equi-angularly relative to one another in a ring pattern. In one example, the magnetic sensors 906 are disposed radially in an overlapping relationship with the outer circumferential edge 902A of the magnetized ring 902 such that a portion of the magnetic sensor 906 resides over the magnetized ring 902 and the remaining portion resides outside the magnetized ring 902.

Figure 13:
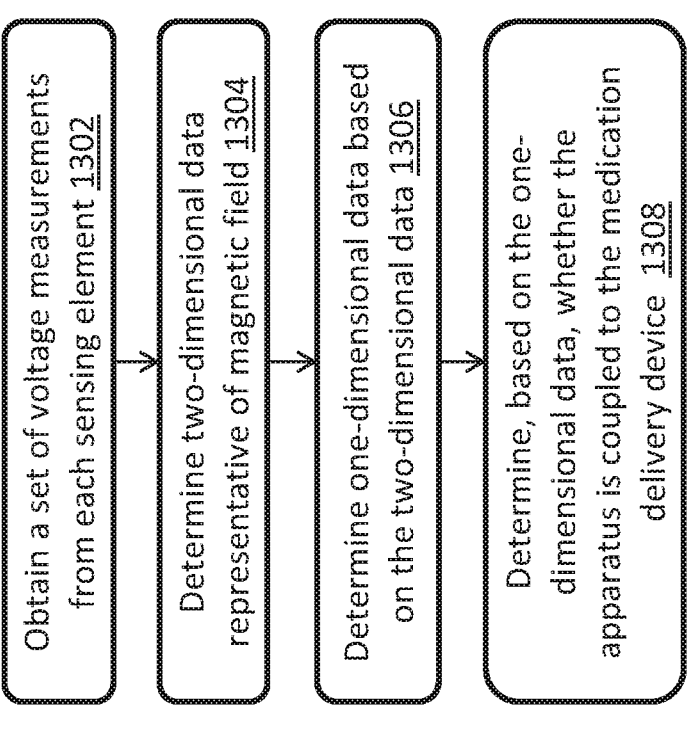
FIG. 13 shows an exemplary computerized method for determining whether the apparatus is removably coupled to a medication injection device, according to some embodiments.

In some embodiments, the sensing system is configured to determine whether the sensing system is coupled to a medication delivery device. FIG. 13 shows an exemplary computerized method 1300 for determining whether the apparatus is removably coupled to a medication injection device, according to some embodiments. The sensing system, such as the dose delivery detection system, includes a plurality of sensing elements. For example, the sensing system includes a number of sensing elements, such as four or five sensing elements, that are equi-circumferentially and equi-radially spaced within the apparatus. As described herein, the plurality of sensing elements can include a plurality of Hall effect sensors. In some embodiments, five Hall effect sensors are equally spaced at 72 degrees apparat around a circle with a diameter designed based on the magnetic component of the medication delivery device being sensed. For example, a diameter of approximately 14 mm can be used such that the sensors insist on an envelope described by the maximum of the Z component of the magnetic field when the magnet rotates around its axis. The sensing system also includes a processor (e.g., MCU) in communication with the set of sensing elements.

The sensing system (via its processor, MCU, etc.) is configured to execute computer-readable instructions that cause the processor to execute the computerized method 1300. At step 1302, the sensing system obtains a set of voltage measurements from each of the plurality of sensing elements. At step 1304, the sensing system determines two-dimensional data representative of a magnetic field of a magnetic component of the medication injection device. At step 1306, the sensing system determines one-dimensional data based on the two-dimensional data. At step 1308, the sensing system determines, based on the one-dimensional data, whether the set of voltage measurements is indicative of the apparatus being coupled to the medication injection device.

Referring to step 1302, when a power on button to the sensing system is pressed by the user, the sensing system is woken up and the firmware running on the processor switches on the sensing elements (e.g., magnetic sensors) in order to take the starting position of the magnetic component of the medication delivery device (e.g., before any rotation takes place). During this phase it is important to take the sensors reading shortly after wake-up, to avoid taking measurements during rotation. In some embodiments, the sensing system can average a number of samples of each sensor (e.g., 5, 10, 15, etc. of each sensor), e.g., to reduce noise.

Referring to step 1304, in some embodiments the sensing system determines a quadrature signal comprising an inphase (I) part and a quadrature (Q) part. The system can determine the I and Q values based on a summation of each sensor value. In some embodiments, the sensing system uses coefficients when summing the sensor values. For example, the system can store one or more coefficients for each sensor. In some embodiments, the sensing system stores one coefficient for each sensor that the sensor value is multiplied by during the summation to determine the I value, and a second coefficient for each sensor that the sensor value is multiplied by during the summation to determine the value. In some embodiments, the coefficients can be used to combine the results of the multiple sensors (e.g., such as five sensors equally spaced at 72 degrees from each other) for the I and Q calculation. In some embodiments, the coefficients can be obtained by solving a system of equations that force the results of the quadrature calculation to have zero error compared to the nominal angle, in front of offset, 2nd harmonic distortion, 3 harmonic distortion in the measured signal, and/or the like.

Referring to step 1306, in some embodiments the sensing system determines a scale factor based on the two-dimensional signal (e.g., the quadrature signal) determined at step 1304. In some embodiments, the sensing system determines the scale factor based on the quadrature signal and one or more of a predetermined offset and a predetermined gain. For example, the processor can determine the scale factor based on the following Equation 12:

$$ScaleFactor = \sqrt{\left(\frac{I - OI}{GI}\right)^2 + \left(\frac{Q - OQ}{GQ}\right)^2} \qquad \text{(Equation 12)}$$

Where:
ScaleFactor is the scale factor;
I is the inphase part of the quadrature signal;
Q is the quadrature part of the quadrature signal;
OI is an offset measured on the I signal during calibration;
OQ is an offset measured on the Q signal during calibration;
GI is a gain measured on the I signal during calibration; and
GQ is a gain measured on the Q signal during calibration.

Such exemplary I and Q offsets and gains can be used since quadrature works well when I and Q are well balanced, such as with an offset equal to zero and a gain equal to one. The calibration process can be used to determine offsets/gains that balance the measured I and Q to achieve sufficient values, to remove skew between I and Q, and/or the like. In some embodiments, the sensing system can be configured to normalize the I and Q values, and to use the I and Q values to determine the normalized angle of the Z component of the magnetic field. After a dose is administered, the sensing system can then monitor the ending position of the magnetic component of the medication delivery device to determine the amount of injected dose (e.g., using similar techniques as described herein to monitor the rotation of the magnet and/or to determine the ending position of the magnet).

Referring to step 1308, the sensing system can determine whether the one-dimensional data is indicative of the sensing system being coupled (or not being coupled) to a medication delivery device. The sensing system can use the scale factor to determine whether the sensing system is mounted or coupled to the medication delivery device. For example, if the scale factor is between predetermined thresholds, then the sensing system can determine that the sensing system is mounted to the medication delivery device. If the scale factor is not between the predetermined thresholds, the sensing system can determine that the sensing system is likely not mounted to the medication delivery device. In some embodiments, the sensing system can check the scale factor against a low amplitude margin and a high amplitude margin to determine whether the magnet that the module is monitoring is the expected magnet (e.g., where +/−25% around nominal is acceptable) so that only a desired amplitude will be accepted by the module.

The dose detection systems have been described by way of example with particular designs of a medication delivery device, such as a pen injector. However, the illustrative dose detection systems may also be used with alternative medication delivery devices, and with other sensing configurations, operable in the manner described herein. For example, any one or more of the various sensing and switch systems may be omitted from the module.

The various methods or processes outlined herein may be coded as software that is executable on one or more processors that employ any one of a variety of operating systems or platforms. Additionally, such software may be written using any of numerous suitable programming languages and/or programming or scripting tools, and also may be compiled as executable machine language code or intermediate code that is executed on a virtual machine or a suitable framework.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms "program," "software," and/or "application" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in non-transitory computer-readable storage media in any suitable form. Data structures may have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more methods, of which examples have been provided. The acts performed as part of a method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This allows elements to optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

What is claimed is:

1. An apparatus configured to determine illumination data indicative of a color of an object, the apparatus comprising:
a set of light emitting diodes (LEDs) in optical communication with the object;
a light sensor in optical communication with the object;
a processor configured to execute computer-readable instructions that cause the processor to:
cause the light sensor to capture illumination data of the object while the object is illuminated by the set of LEDs;
process the illumination data to generate processed illumination data, comprising one or more of:
adjusting the illumination data based on a temperature associated with the object; and
normalizing the illumination data based on a set of normalization parameters; and
transmit, using a transmitter or transceiver in communication with the processor, the processed illumination data to a remote device.

2. The apparatus of claim 1, wherein the light sensor is an ambient light sensor.

3. The apparatus claim 1, wherein the object is a portion of a medication delivery device that can be used to identify an aspect of the medication delivery device based on the color of the object.

4. The apparatus of claim 1, further comprising a light guide disposed between (a) the set of LEDs, the light sensor, or both, and (b) the object.

5. The apparatus of claim 1, wherein causing the light sensor to capture illumination data of the object while the object is illuminated by the set of LEDs comprises causing the light sensor to capture:
first illumination data when the object is not illuminated by the set of LEDs; and
second illumination data when the object is illuminated by each LED of the set of LEDs.

6. The apparatus of claim 5, wherein:
the set of LEDs comprises a red LED, a blue LED, and a green LED; and
causing the light sensor to capture the second illumination data comprises:
causing the light sensor to capture (a) third illumination data when the object is illuminated by the red LED; (b) fourth illumination data when the object is illuminated by the green LED; and (c) fifth illumination data when the object is illuminated by the green LED.

7. An apparatus configured to determine a battery indicator indicative of a remaining life of a battery, the apparatus comprising:
a set of light emitting diodes (LEDs) in optical communication with an object, and a light sensor in optical communication with the object, the object comprising a portion of a medication delivery device;
a battery;
a temperature sensor;
a processor in communication with the set of LEDs, the light sensor, the battery and the temperature sensor, the processor being configured to execute computer-readable instructions that cause the processor to:
cause the light sensor to capture illumination data of the object while the object is illuminated by the set of LEDs;
obtain a set of voltage measurements of the battery;
obtain, via the temperature sensor, a temperature measurement;
determine a set of temperature-adjusted battery indications based on the temperature measurement; and
determine a battery indicator indicative of a remaining life of the battery based on the temperature-adjusted battery indications and the set of voltage measurements.

8. The apparatus of claim 7, wherein obtaining the set of voltage measurements comprises:
obtaining a startup battery voltage when the apparatus is powered on;
obtaining a high current battery voltage when the processor is running at a maximum speed; and
obtaining a low current battery voltage when the processor is running in a low-power mode.

9. The apparatus of claim 7, wherein determining the set of temperature-adjusted battery indications based on the temperature measurement comprises:
storing:
a set of low temperature battery indications, wherein each low temperature battery indication comprises a battery indication and an associated voltage for a low temperature; and
a set of high temperature battery indications, wherein each high temperature battery indication comprises a battery indication and an associated voltage for a high temperature; and
determining, based on the set of low temperature battery indications, the set of high temperature battery indications, and the temperature measurement, the set of temperature-adjusted battery indications.

10. The apparatus of claim 9, wherein determining the battery indicator indicative of the remaining life of the battery comprises:
obtaining a previous battery indicator for the battery;
determining a current battery indicator for the battery based on the temperature-adjusted battery indications and the set of voltage measurements;
determining the battery indicator based on the previous battery indicator and the current battery indicator.

11. The apparatus of claim 7, further comprising transmitting the battery indicator to a remote device.

12. The apparatus of claim 1, further comprising a battery; a temperature sensor, wherein the processor is in communication with the battery and the temperature sensor, the processor being configured to execute computer-readable instructions that cause the processor to:

obtain an electrical measurement of the battery;

obtain, via the temperature sensor, a temperature measurement;

determine a set of temperature-adjusted battery indications based on the temperature measurement; and determine a battery indicator indicative of a remaining life of the battery based on the temperature-adjusted battery indications and the set of electrical measurements.

13. The apparatus of claim 1, further comprising a plurality of sensing elements, wherein the processor is in communication with the sensing elements, the processor being configured to execute computer-readable instructions that cause the processor to:

obtain a set of electrical measurements from each of the plurality of sensing elements;

determine two-dimensional data representative of a magnetic field of a magnetic component of the medication injection device;

determine one-dimensional data based on the two-dimensional data; and determine, based on the one-dimensional data, whether the set of voltage measurements is indicative of the apparatus being coupled to the medication injection device.

14. The apparatus of claim 13, further comprising a battery; a temperature sensor, wherein the processor is in communication with the battery and the temperature sensor, the processor being configured to execute computer-readable instructions that cause the processor to:

obtain an electrical measurement of the battery; obtain, via the temperature sensor, a temperature measurement;

determine a set of temperature-adjusted battery indications based on the temperature measurement; and determine a battery indicator indicative of a remaining life of the battery based on the temperature-adjusted battery indications and the set of electrical measurements.

\* \* \* \* \*